United States Patent
Jiang et al.

(10) Patent No.: US 11,377,418 B2
(45) Date of Patent: Jul. 5, 2022

(54) COMPOUNDS AND METHODS FOR TREATING INFLUENZA

(71) Applicant: Macau University of Science and Technology, Taipa (MO)

(72) Inventors: Zhi-Hong Jiang, Taipa (MO); Nanshan Zhong, Taipa (MO); Zifeng Yang, Taipa (MO); Jingrong Wang, Taipa (MO); Qitong Feng, Taipa (MO); Xiaobo Zhou, Taipa (MO); Beixian Zhou, Taipa (MO)

(73) Assignee: Macau University of Science and Technology, Taipa (MO)

( * ) Notice: Subject to any disclaimer, the term of this patent is extended or adjusted under 35 U.S.C. 154(b) by 0 days.

(21) Appl. No.: 17/110,567

(22) Filed: Dec. 3, 2020

(65) Prior Publication Data
US 2022/0127220 A1  Apr. 28, 2022

(30) Foreign Application Priority Data
Oct. 28, 2020  (CN) .......................... 202011174804.5

(51) Int. Cl.
*C07C 233/87* (2006.01)
(52) U.S. Cl.
CPC ................... *C07C 233/87* (2013.01)
(58) Field of Classification Search
CPC .................................................. C07C 233/87
USPC ........................................................ 514/506
See application file for complete search history.

(56) References Cited

U.S. PATENT DOCUMENTS 9,023,809 B2 * 5/2015 Liang ................... C07C 235/32
514/21.91

* cited by examiner

*Primary Examiner* — Deborah D Carr
(74) *Attorney, Agent, or Firm* — Renner Kenner Greive Bobak Taylor & Weber

(57) ABSTRACT

A compound including a structure of Formula (I) and a preparation method thereof, Formula (I)

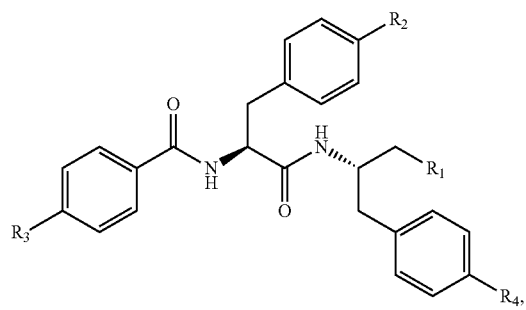

wherein $R_1$ is —OH, —CH$_2$OH, or —OCOCH$_3$; $R_2$, $R_3$, and $R_4$ are independently —H, —CH$_3$ or —F, and at least one of $R_2$, $R_3$, and $R_4$ is —F. A method for treating a subject suffering from a viral disease includes administering an effective amount of said compound or a solvate thereof to the subject.

27 Claims, 2 Drawing Sheets

COMPOUNDS AND METHODS FOR TREATING INFLUENZA

TECHNICAL FIELD

The present invention relates to compounds and methods useful for treating a viral disease particularly but not exclusively influenza. Compounds of the present invention particularly carry at least one fluorine atom and are found to be useful against influenza virus. The present invention also relates to a method of preparing the compounds.

BACKGROUND

Seasonal influenza is an acute respiratory infection caused by influenza viruses and is one of the leading causes of high morbidity and mortality worldwide. Influenza is a disease with a high mortality rate throughout the world and the effects of vaccines against influenza virus infection are limited due to the frequent variation of viral antigens.

Influenza viruses have various types including types A, B and C. The type A influenza virus (influenza A virus) causes influenza in mammals and birds, can cause epidemic or pandemic infections. Influenza A viruses have several subtypes depending on the type of certain viral proteins, and those that are able to cross-infect and recombine between different species are the most virulent human pathogens. Several severe influenza pandemics were caused by, for example, the subtypes H1N1, H3N2 or HN1.

Although the existing therapeutic drugs, including amantadine, rimantadine, zanavir, and oseltamivir, are able to reduce the severity and duration of the illness, the occurrence of resistant influenza A viruses is inevitable. Due to mutation or assortment of the viral genome, the ineffectiveness of currently available anti-viral drugs (such as amantadine and oseltamivir) highlights the urgent need for the development of new antiviral compounds.

Thus, there is a strong need for therapeutically effective compounds and improved methods for treating influenza, especially infections caused by influenza A virus.

SUMMARY OF THE INVENTION

In one aspect of the present invention, there is provided a compound comprising a structure of Formula (I)

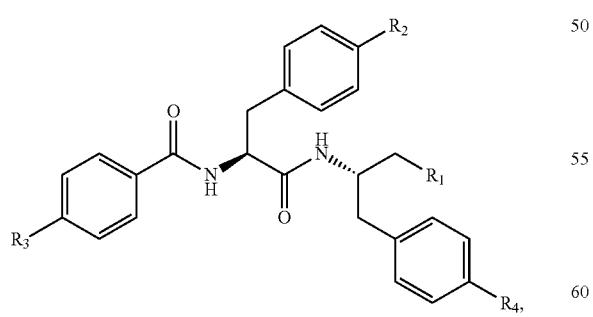

Formula (I)

wherein $R_1$ is —OH, —CH$_2$OH, or —OCOCH$_3$;
$R_2$, $R_3$, and $R_4$ are independently —H, —CH$_3$ or —F, and at least one of $R_2$, $R_3$, and $R_4$ is —F.

In embodiments, $R_1$ of the compound is —OH, or —OCOCH$_3$, and/or at least two of $R_2$, $R_3$, and $R_4$ of the compound are —F. In a particular embodiment, $R_2$, $R_3$, and $R_4$ of the compound are simultaneously —F.

In an embodiment, the compound has a structure selected from the group consisting of Formula (IIb) to Formula (IIh)

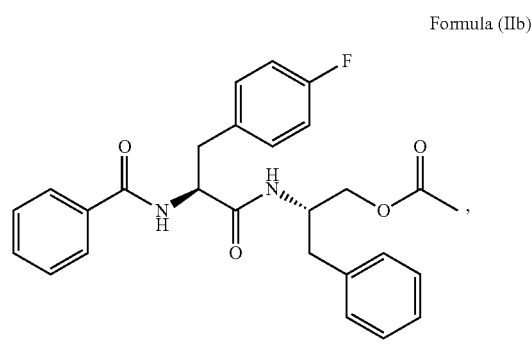

Formula (IIb)

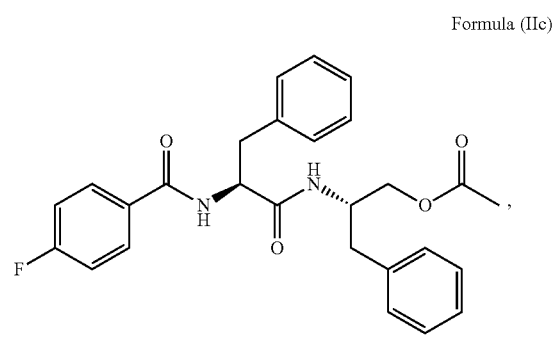

Formula (IIc)

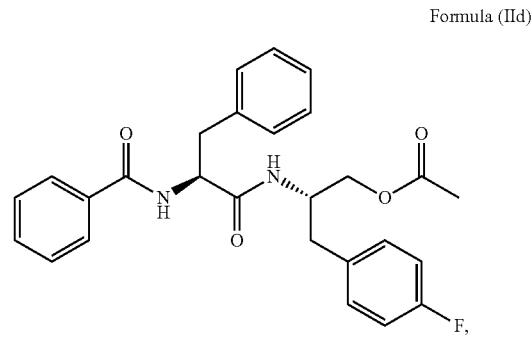 [SMILES: CC(=O)OC[C@H](Cc1ccc(F)cc1)NC(=O)[C@H](Cc1ccccc1)NC(=O)c1ccccc1]

Formula (IId)

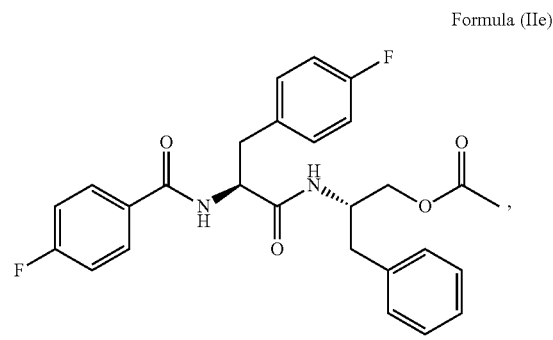

Formula (IIe)

Formula (IIf)
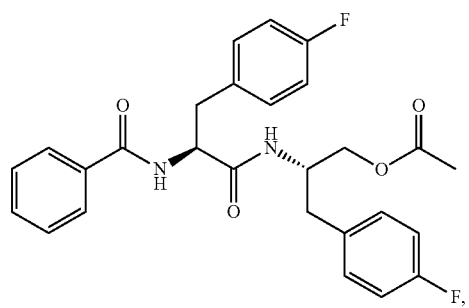
Formula (IIg)
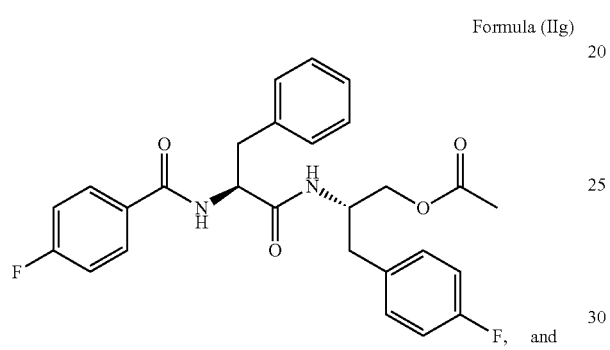
, and
Formula (IIh)
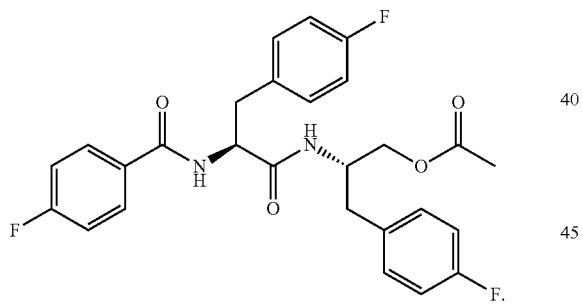
In another embodiment, the compound has a structure selected from the group consisting of Formula (IIIb) to Formula (IIIh)
Formula (IIIb)
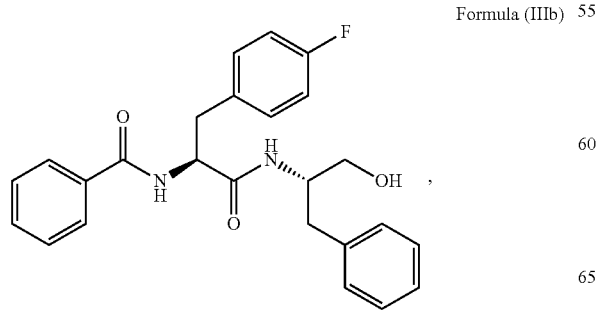
,
Formula (IIIc)
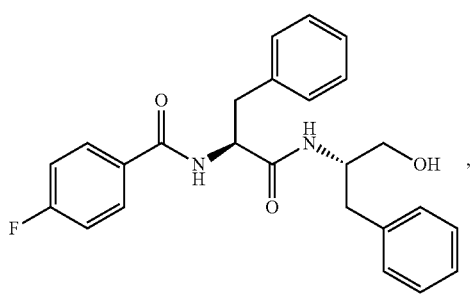
,
Formula (IIId)
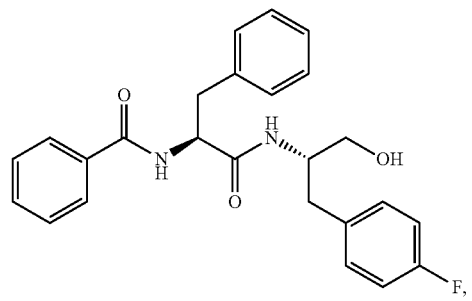
,
Formula (IIIe)
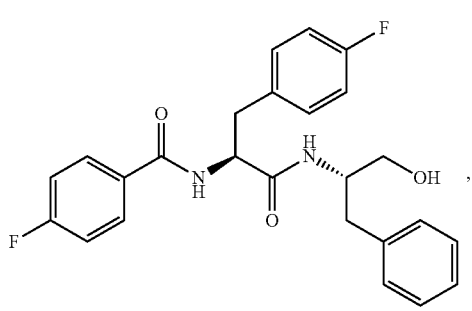
,
Formula (IIIf)
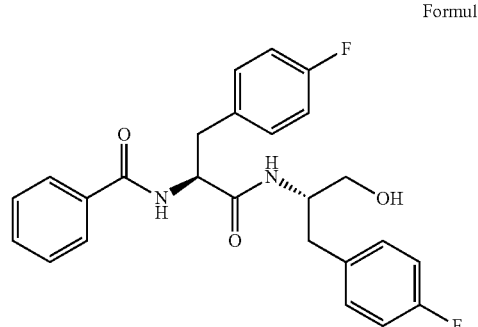
,
Formula (IIIg)
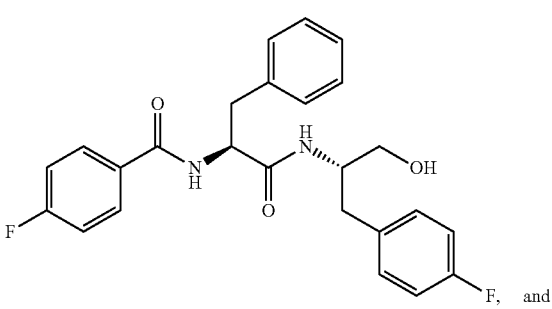
, and

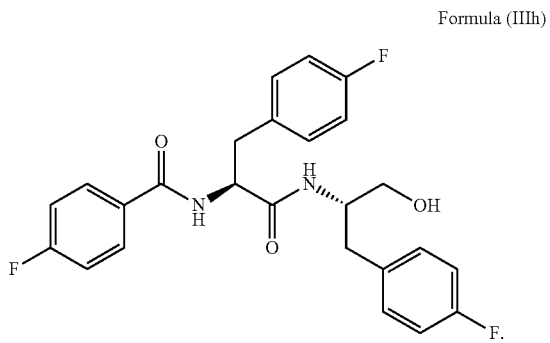 [SMILES: O=C(N[C@@H](Cc1ccc(F)cc1)C(=O)N[C@H](CO)Cc1ccc(F)cc1)c1ccc(F)cc1]

Formula (IIIh)

In another aspect of the present invention, there is provided a method of treating a subject suffering from a viral disease, particularly influenza, comprising administering an effective amount of said compound to the subject.

In a further aspect of the present invention, there is provided a method of preparing said compound. The method comprises steps of:

a) contacting a N-Cert-butoxycarbonyl-protected amino acid (N-Boc-protected amino acid) of Formula (IV) with an amino alcohol of Formula (V), optionally in the presence of a coupling agent, under suitable condition to form a first intermediate of Formula (VI),

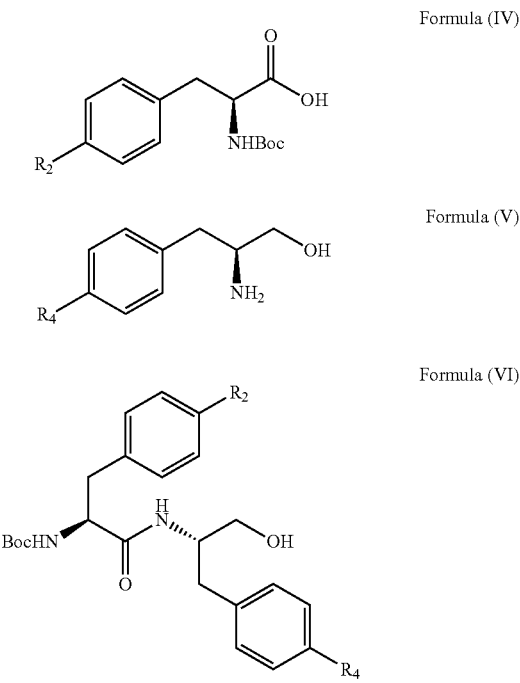

Formula (IV)

Formula (V)

Formula (VI)

wherein $R_2$ and $R_4$ are independently —H, —CH$_3$ or —F, b) converting the first intermediate into an ester;

c) removing a Boc group from the ester of the step b) to form a second intermediate; and d) contacting the second intermediate with a substituted or unsubstituted benzoyl chloride of Formula (VII) to form the compound

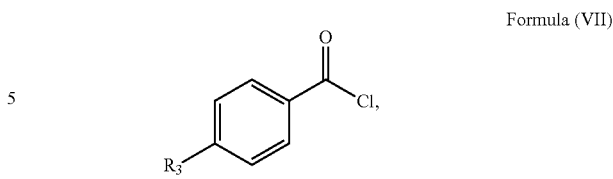

Formula (VII)

wherein $R_3$ is —H, —CH$_3$ or —F.

The compounds of the present invention are derived from aurantiamide and aurantiamide acetate and they are found to have anti-viral effect particularly against influenza virus A. Some of them also exhibit strong inhibitory effect against NF-κB activation. The anti-viral effect of the compounds may be associated with the NF-κB signalling pathway. The compounds herein are suitable for the treatment of a viral disease particularly influenza. Accordingly, the present invention at least provides suitable alternative for treating influenza A infection, and may be useful against drug-resistant strains of influenza.

Other features and aspects of the invention will become apparent by consideration of the following detailed description and accompanying drawings.

BREW DESCRIPTION OF THE DRAWINGS

DESCRIPTION OF THE EMBODIMENTS

Figure 1:
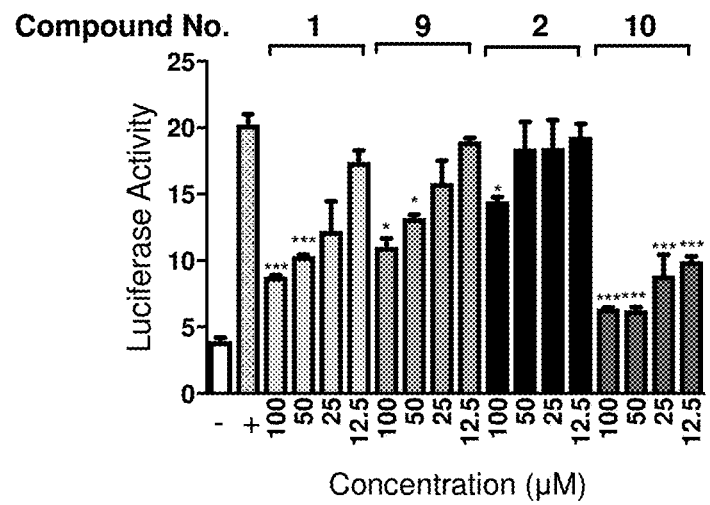
FIG. 1 is a plot showing the luciferase activity of TNF-α-induced HEK293 cells treated respectively with Compound 1, Compound 2, Compound 9 and Compound 10 at a concentration of 100 μM, 50 μM, 25 μM, or 12.5 μM, *p<0.05, p<0.01, *p<0.001, compared to TNF-a-treated alone.

Unless otherwise defined, all technical claims used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components. "Consisting of" means that the material is solely consist of, i.e. is formed by the respective element. As used herein, the forms "a", "an", and "the" are intended to include the singular and plural forms unless the contest indicates otherwise.

According to the present invention, there is provided a compound which is useful in treating a viral disease particularly influenza. The compound comprises a structure of Formula (I)

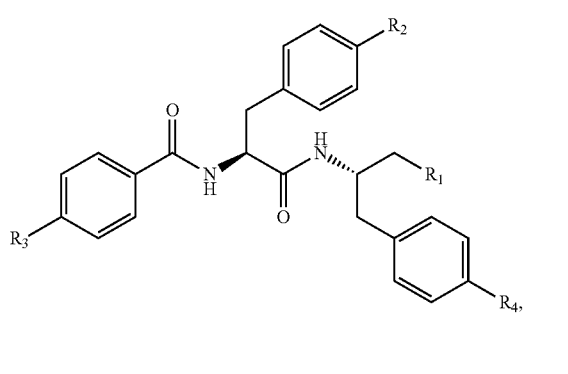

Formula (I)

wherein $R_1$ is —OH, —CH$_2$OH, or —OCOCH$_3$; $R_2$, $R_3$, and $R_4$ are independently —H, —CH$_3$ or —F, and at least one of $R_2$, $R_3$, and $R_4$ is —F.

In embodiments, $R_1$ of the compound is —OH or —OCOCH$_3$, and $R_2$, $R_3$, and $R_4$ are as defined above. $R_2$, $R_3$, and $R_4$ may be independently —H, or —F with at least one of them being —F.

The compound is preferably a fluorinated compound having at least one fluorine atom linked to a phenyl ring, i.e. at least one hydrogen atom of the phenyl ring is substituted with a fluorine atom. The fluorine atom is preferably present at the para-position of the ring. In an embodiment, at least two of $R_2$, $R_3$, and $R_4$ are —F, and the remaining one is —H or —CH$_3$ preferably —H. In an alternative embodiment, $R_2$, $R_3$, and $R_4$ are all simultaneously —F.

It would be appreciated that the compound is not an aurantiamide acetate having a structure of Formula (IIa) or an aurantiamide having a structure of Formula (IIIa). Aurantiamide acetate and aurantiamide do not have a halogen atom such as a fluorine atom.

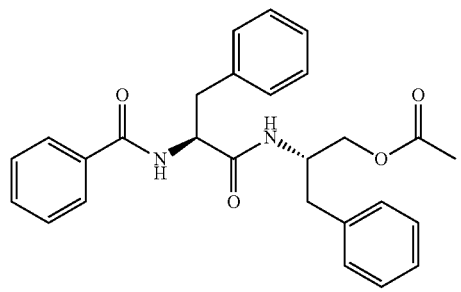

Formula (IIa)

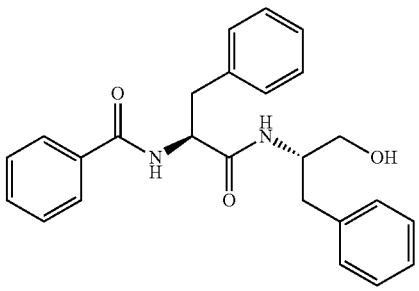

Formula (IIIa)

In embodiments, the compound of the present invention has a structure selected from the following formulas.

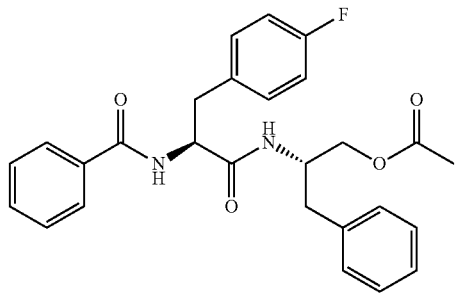

Formula (IIb)

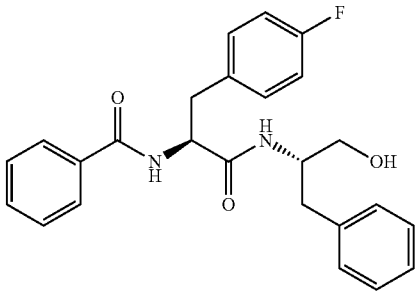

Formula (IIIb)

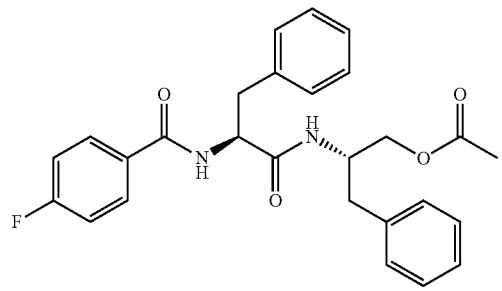

Formula (IIc)

Formula (IIIc)
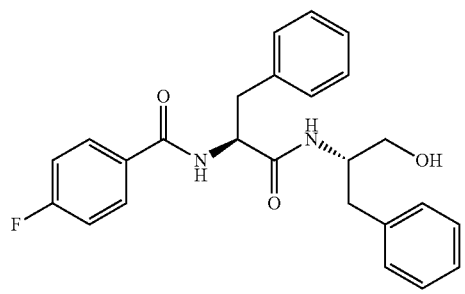
Formula (IId)
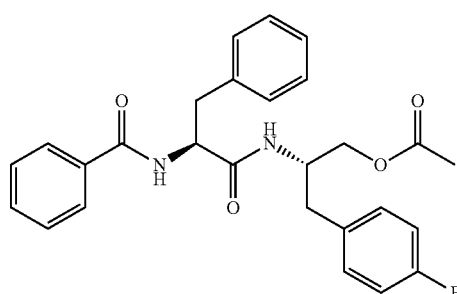
Formula (IIId)
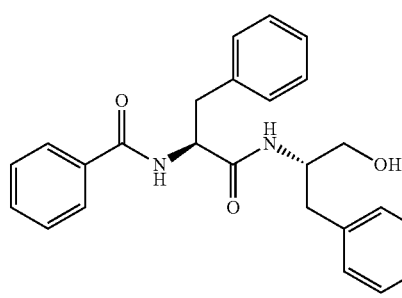
Formula (IIe)
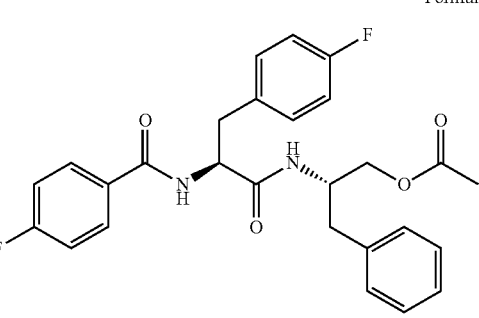
Formula (IIIe)
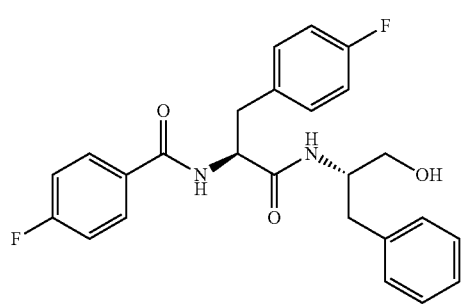
Formula (IIf)
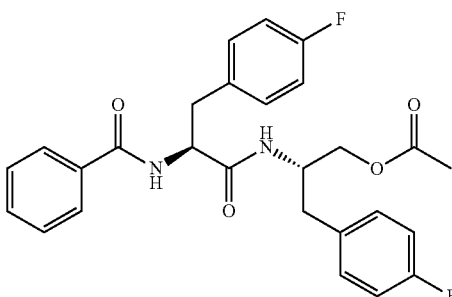
Formula (IIIf)
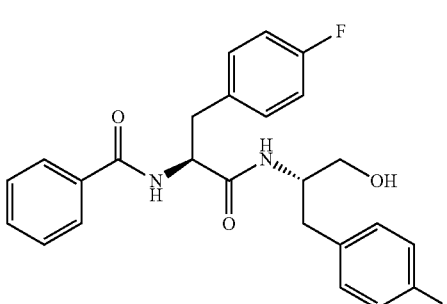
Formula (IIg)
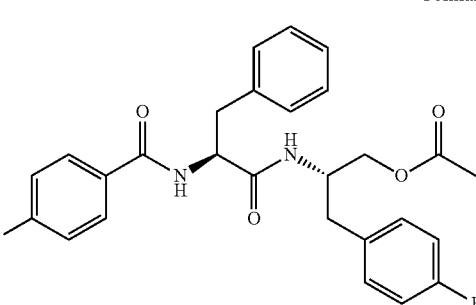
Formula (IIIg)
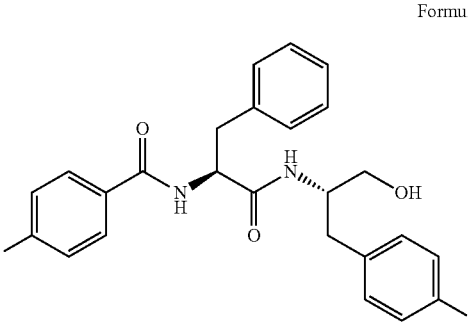
Formula (IIh)
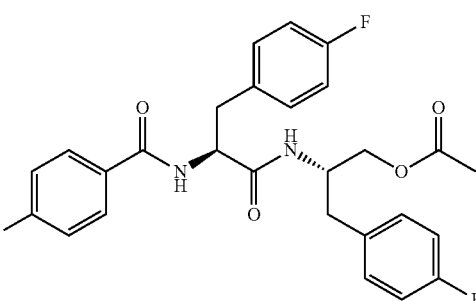

Formula (IIIh)

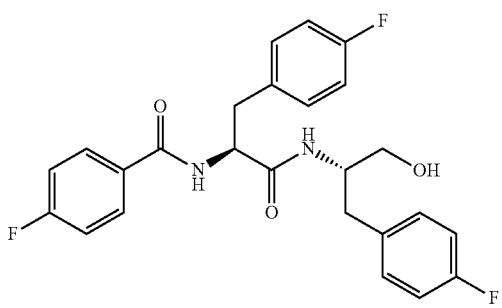

The inventors found that these compounds have inhibitory effect against a virus particular influenza virus, and therefore these compounds may be developed as anti-viral agents for treating a viral disease such as influenza which is described in detail in the later part and in the examples.

In one embodiment, the compound has a structure selected from the group consisting of Formula (IIb) to Formula (IIh) as shown above. In another embodiment, the compound has a structure selected from the group consisting of Formula (IIIb) to (IIIh) as shown above. Particularly, the compound has a structure of Formula (IIf) or (IIIf) which has an inhibitory effect on NF-κB activation. In another embodiment, the compound has a structure of Formula (IIh) or (IIIh).

The compound as described above can be prepared by chemical synthesis. Therefore, the present invention also pertains to a method of preparing the compound of the present invention, and the compound is as described above. The method comprises contacting a substituted or unsubstituted N-tert-butoxycarbonyl-protected amino acid (N-Boc-protected amino acid) with a substituted or unsubstituted amino alcohol for reaction to occur, particularly for condensation to form an intermediate; converting the intermediate into an ester, and replacing the N-Boc-protected group of the ester with a substituted or unsubstituted benzoyl group.

Preferably, each of the N-Boc-protected amino acid and the amino alcohol contains an aromatic ring which may be substituted with a halogen atom preferably a fluorine atom. More preferably, the fluorine atom is at the para-position of the aromatic ring. In an embodiment, the benzoyl group is substituted with a halogen atom preferably a fluorine atom particular at the para-position.

In embodiments where the compound has a structure of Formula (I) in which $R_1$ is —OH or —OCOCH$_3$, and $R_2$, $R_3$, and $R_4$ are independently —H, —CH$_3$ or —F with at least one of them being —F, the method comprises the steps of:
a) contacting a N-tert-butoxycarbonyl-protected amino acid (N-Boc-protected amino acid) of Formula (IV) with an amino alcohol of Formula (V), optionally in the presence of a coupling agent, under suitable condition to form a first intermediate of Formula (VT), Formula (IV)

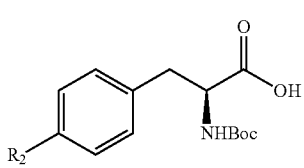

Formula (V)

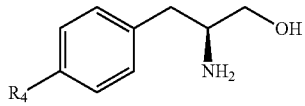

Formula (VI)

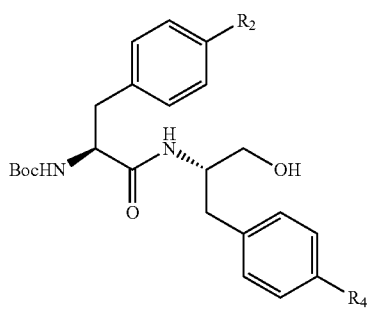

wherein $R_2$ and $R_4$ are independently —H, —CH$_3$ or —F, b) converting the first intermediate into an ester;
c) removing the tert-butoxycarbon (Boc) group from the ester of the step b) to form a second intermediate; and
d) contacting the second intermediate with a substituted or unsubstituted benzoyl chloride of Formula (VII) to form the compound Formula (VII)

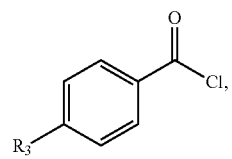

wherein $R_3$ is —H, —CH$_3$ or —F.

In embodiments, $R_2$, $R_3$ and $R_4$ of the above components are independently —H, or —F, if present.

In the step a), the coupling agent may be 1-ethyl-3-(3-dimethylaminopropyl) carbodiimide (abbreviated as EDCI) and/or hydroxybenzotriazole (abbreviated as HOBT). The coupling agent assists the adhesion between the N-Boc-protected amino acid and the amino alcohol for condensation to occur efficiently. Preferably, the condensation reaction takes place at room temperature, or at an elevated temperature, for about or more than 12 hours, about or more than 18 hours, about or more than 24 hours.

Optionally, the step a) further comprises a purification step to purify the first intermediate before subsequent reaction or steps.

A solvent may be used to dissolve all the components for the reaction in the step a). Preferably, the solvent is an organic solvent such as dichloromethane (abbreviated as DCM). A person skilled in the art would appreciate other suitable solvents for the same process as described herein.

In the step b), the first intermediate may be converted into the ester by contacting with a carboxylic acid anhydride, particularly acetic anhydride, to form the ester of Formula (VIII)

Formula (VIII)

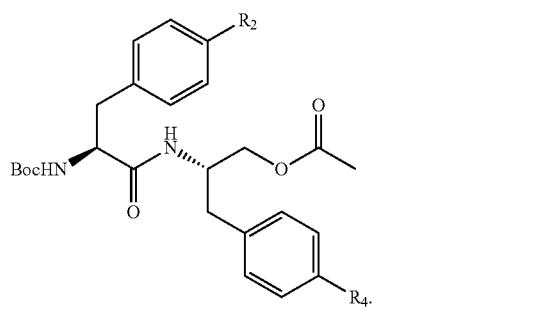

In the step c), the Boc group may be removed from the ester by using an acid to form the second intermediate of Formula (IX)

Formula (IX)

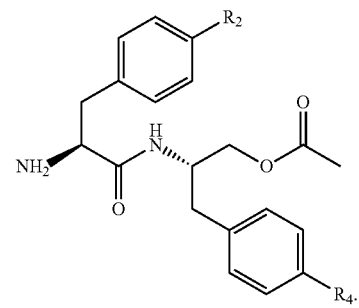

Preferably, the acid is a hydrochloric acid or a carboxylic acid that is strong enough to remove the Boc group. The carboxylic acid may be a perfluorinative carboxylic acid, preferably trifluoroacetic acid ($CH_3COOH$).

The step c) may further comprise a purification to purify the second intermediate prior to the step d).

In the step d), the second intermediate is subjected to amidation with the substituted or unsubstituted benzoyl chloride to form the compound of the present invention, in the presence of an organic solvent particularly DCM. Preferably, the resultant compound obtained in the step d) has the following structure:

Formula (X)

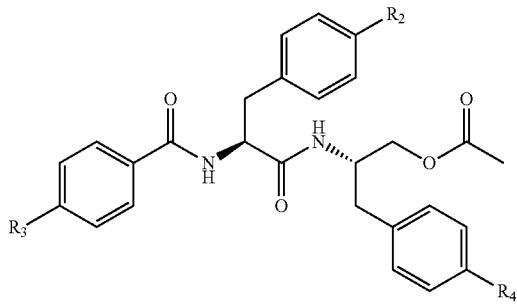

wherein $R_2$, $R_3$, and $R_4$ are independently —H, —$CH_3$ or —F with at least one of them being —F. In an embodiment, the compound prepared according to method herein has a structure selected from Formula (IIb) to (IIh).

In an alternative embodiment, the resultant compound having a structure of Formula (X), or Formula (IIb) to (IIh), is further subjected to ester hydrolysis by using a reducing agent such as, but not limited to, lithium aluminum hydride ($LiAlH_4$) to produce the compound of Formula (XI)

Formula (XI)

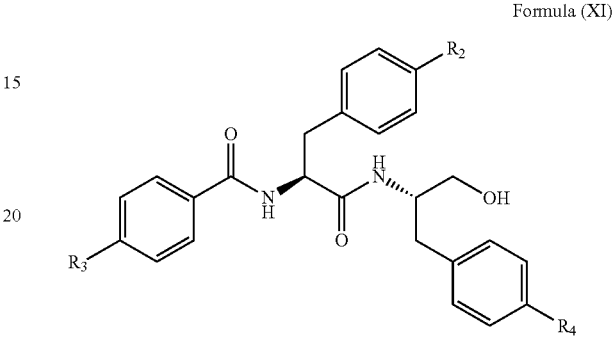

wherein $R_2$, $R_3$, and $R_4$ are independently —H, —$CH_3$ or —F with at least one of them being —F. In an embodiment, the compound prepared according to method has a structure selected from Formula (IIIb) to (IIIh).

The compound prepared according to the method herein thus has at least one fluorine atom at the phenyl ring of benzoyl, phenylalanine, or phenylalaninol of the compound. The method of the present invention does not require stringent conditions and can produce the desired compounds in a convenient manner. It would be appreciated that the method disclosed herein may be modified for mass production. The compound of the present invention may be modified as a prodrug or other form that is suitable for packaging, storage and/or applications, to achieve the desired effect as described in the present disclosure.

In another aspect, the present invention pertains to a method of treating a subject suffering from a viral disease, particularly influenza, especially an infection caused by influenza A virus. The method comprises a step of administering an effective amount of the compound of Formula (I) or a solvate thereof to the subject. The compound is as described above.

The viral disease is preferably caused by a RNA virus, i.e. a virus containing a RNA molecule as its genetic material. More preferably, the viral disease is influenza, i.e. an infection caused by an influenza virus. In embodiments, the influenza virus is influenza A virus including, but not limited to, subtypes H1N1, H3N2, and H5N1. Particularly, the viral disease is caused by influenza A virus subtype H1N1.

In embodiments, the compound has a structure selected from the group consisting of Formula (IIb) to (IIh), (IIIb) to (IIIh). Particularly, the compound may have a structure of Formula (IIf), (IIg), (IIh), (IIIb), (IIIe), (IIIf), or (IIIh). In an embodiment, the compound has a structure of Formula (IIf), (IIh), (IIIf), or (IIIh). It would be appreciated that solvates of the compound are also included in the scope, and may be used for treating the same virus infection. Examples of a solvate include a hydrate, ethanol solvate, and acetone solvate.

The term "subject" in particular refers to an animal or human, in particular a mammal and most preferably human.

In an embodiment, the subject is susceptible to or is suffering from a viral disease particularly influenza.

The expression "effective amount" generally denotes an amount sufficient to produce therapeutically desirable results, wherein the exact nature of the result varies depending on the specific condition which is treated. When the disorder is a viral disease, the result is usually an inhibition of the replication of the virus, a prevention or suppression of the virus-induced cytopathic effects, a boost in the immune system of the subject against the entry of the virus, an inhibition of the interaction between the host cells and the virus, and/or the combinations thereof.

The effective amount of the compound may depend on the $IC_{50}$, the species, body weight, age and individual conditions of the subject and can be determined by standard procedures such as with cell cultures or experimental animals.

The compound may be provided in a pharmaceutical composition which can be formulated in solid, semisolid or liquid form to be administered by an oral, rectal, topical, parenteral or transdermal or inhalative route to a subject, preferably a human. The skilled person is able to select suitable pharmaceutically tolerable excipients depending on the form of the pharmaceutical composition and is aware of methods for manufacturing pharmaceutical compositions as well as able to select a suitable method for preparing the pharmaceutical composition depending on the kind of pharmaceutically tolerable excipients and the form of the pharmaceutical composition.

The pharmaceutical composition may comprise more than one compound of the present invention, i.e. the compounds can be used in combination with each other. Alternatively, the pharmaceutical composition may comprise other pharmaceutical effective ingredients such as therapeutic compounds used for treating viral diseases in particular influenza, including amantadine, oseltamivir, rimantadine, zanavir, ribavirin, and the like.

It would be appreciated that the present invention relates to use of the compound as described above in treatment of a viral disease as described above, and use in the preparation of a medicament for treating of said viral disease. A person having ordinary skills in the art would appreciate suitable methods to prepare a medicament for the intended purposes based on the disclosure herein.

EXAMPLES

Example 1

Synthesis of Compounds

Different compounds of the present invention were prepared according to the following approach. 0.36 g of Tert-butoxycarbonyl protecting group-L-amino acid (Boc-L-amino acid) and 0.21 g L-phenylalaninol were mixed in a solution with 10 ml dichloromethane ($CH_2Cl_2$), and coupling agents including 0.29 g of EDCI and 0.19 g of HOBT (EDCI:HOBT=1:1) were added to the mixture successively. The reaction mixture was stirred overnight at room temperature. The products were further esterified with 144.4 µL acetic anhydride in 10 mL pyridine, at room temperature. After removing the Boc-protected-group by using $CF_3COOH$ (1 mL) in DCM (9 mL), at room temperature, followed by purification, PhCOCl (60 µL) dissolved in DCM (4 mL) was added. Ester hydrolysis reaction was produced by $LiAlH_4$ (9.2 mg) in THF (4 mL), at room temperature. All the purification was conducted by using column chromatography (Si-Gel) with petroleum ether and n-hexane. The resultant compounds and their properties including spectroscopic data are as follows.

Compound 1

(S)-2-((S)-2-benzamido-3-phenylpropanamido)-3-phenylpropyl acetate

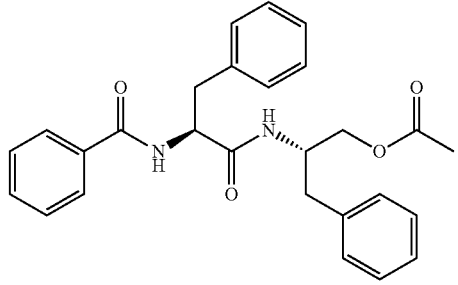

Formula (IIa)

Properties: White powders. Yield: 87%. $[\alpha]_{25}^D$ −12.8 (c=0.620, MeOH); $^1$H-NMR (600 MHz, $CDCl_3$) δ: 7.72 (2H, d, J=7.77 Hz), 7.53 (1H, t, J=7.46 Hz), 7.44 (2H, t, J=7.81 Hz), 7.33-7.31 (2H, m), 7.29-7.28 (2H, m), 7.27-7.25 (1H, m), 7.21-7.19 (2H, m), 7.18-7.16 (1H, m), 7.07 (2H, d, J=8.1 Hz), 6.81 (1H, J=8.4 Hz), 6.02 (1H, J=8.4 Hz), 4.82-4.78 (1H, m), 4.40-4.35 (1H, m), 3.94 (1H, dd, J=11.3, 4.9 Hz), 3.82 (1H, dd, J=11.3, 4.2 Hz), 3.23 (1H, dd, J=13.7, 5.91 Hz), 3.07 (1H, dd, J=13.7, 8.5 Hz), 2.82-2.74 (2H, m), 2.05 (3H, s). $^{13}$C-NMR (150 MHz, $CDCl_3$) δ: 170.8, 170.3, 167.1, 136.7, 136.6, 133.6, 132.0, 129.3, 129.1, 128.8, 128.7, 128.6, 127.2, 127.1, 126.8, 64.6, 55.0, 49.4, 38.4, 37.4, 20.8. TOF-ESI-MS: 467.1810 [M+Na]$^+$ Calcd. for $C_{27}H_{28}N_2O_4$: 444.2049.

Compound 2

(S)-2-((S)-2-(4-fluorobenzamido)-3-phenylpropanamido)-3-phenylpropyl acetate

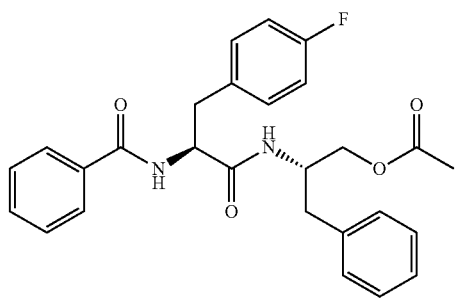

Formula (IIb)

Properties: White powders. Yield: 88%. $[\alpha]_{25}^D$ −10.5 (c=1.14, MeOH); $^1$H-NMR (600 MHz, DMSO-d$^6$) δ: 8.52 (1H, d, J=8.4 Hz), 8.17 (1H, d, J=8.4 Hz), 7.72 (2H, d, J=7.77 Hz), 7.44 (2H, t, J=7.81 Hz), 7.35-7.33 (2H, m), 7.28-7.2-7.25 (2H, m), 7.25-7.24 (1H, m), 7.22-7.15 (2H, m), 7.07 (2H, t, J=8.9 Hz), 4.67-4.65 (1H, m), 4.20-4.15

(1H, m), 4.01 (1H, dd, J=11.3, 4.9 Hz), 3.86 (1H, dd, J=11.3, 4.2 Hz), 3.01 (1H, dd, J=13.7, 5.91 Hz), 2.94 (1H, dd, J=13.7, 8.5 Hz), 2.82-2.75 (2H, m), 1.98 (3H, s), $^{13}$C-NMR (150 MHz, DMSO-d$^6$) δ: 171.5, 170.8, 166.5, 162.2 (d, J=241.2 Hz), 138.4, 134.9 (d, J=2.8 Hz), 134.4, 131.8, 131.4 (d, J=7.8 Hz), 129.6, 128.70, 128.67, 127.9, 126.7, 115.3 (d, J=20.8 Hz), 65.1, 55.3, 49.6, 36.99, 36.85, 21.1. TOF-ESI-MS: 485.1705 [M+Na]$^+$ (calcd. for $C_{27}H_{27}FN_2O_4$: 462.1955).

Compound 3

(S)-2-((S)-2-(4-fluorobenzamido)-3-phenylpropanamido)-3-phenylpropyl acetate

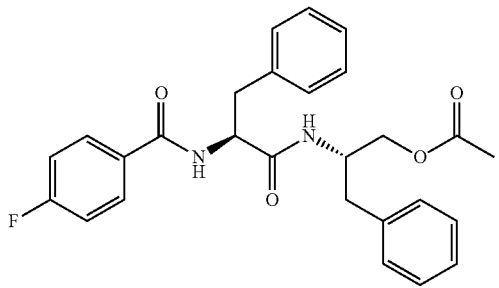

Formula (IIc)

Properties: White powders. Yield: 87%. $[α]_{23}^D$ −6.1 (c=0.66, MeOH); $^1$H-NMR (600 MHz, DMSO-d$^6$) δ: 8.57 (1H, d, J=8.4 Hz), 8.16 (1H, d, J=8.4 Hz), 7.87 (2H, dd. J=8.9, 5.5 Hz), 7.32-7.29 (2H, m), 7.28-7.27 (2H, m), 7.26-7.25 (2H, m), 7.24-7.23 (2H, m), 7.23-7.21 (2H, m), 7.18-7.15 (2H, m), 4.69-4.65 (1H, m), 4.21-4.17 (1H, m), 4.02 (1H, dd, J=11.0, 4.9 Hz), 3.86 (1H, dd, J=11.0, 6.7 Hz), 3.02 (1H, dd, J=13.8, 7.26 Hz), 2.97 (1H, dd, J=13.8, 6.39 Hz), 2.83-2.76 (2H, m), 1.99 (3H, s). $^{13}$C-NMR (150 MHz, DMSO-d$^6$) δ: 171.6, 170.8, 165.5, 165.2 (d, J=248.6 Hz), 138.8, 138.4, 130.9, 130.6 (d, J=8.2 Hz), 129.6, 128.7, 128.5, 126.7 (d, J?=2.2 Hz), 115.6 (d, J=21.6 Hz), 65.1, 55.4, 49.6, 37.7, 37.0, 21.1. TOP-ESI-MS: 485.1718 [M+Na]$^+$ (calcd. for $C_{27}H_{27}FN_2O_4$: 462.1955).

Compound 4

(S)-2-((S)-2-benzamido-3-phenylpropanamido)-3-(4-fluorophenyl)propyl acetate

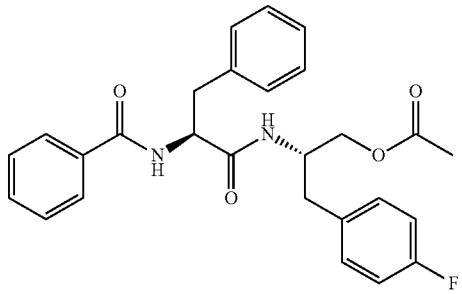

Formula (IId)

Properties: White powders. Yield: 85%. $[α]_{25}^D$ −5.3 (c=0.75, MeOH); $^1$H-NMR (600 MHz, CDCl$_3$) δ: 7.70 (2H, d, J=7.77 Hz), 7.53 (1H, t, J=7.46 Hz), 7.44 (2H, t, J=7.81 Hz), 7.32-7.25 (4H, m), 7.06-7.04 (2H, m), 6.82 (2H, t, J=8.6 Hz), 6.78 (1H, d, J=8.4 Hz), 6.16 (1H, d, J=8.4 Hz), 4.81-4.77 (1H, m), 4.34-4.19 (1H, m), 3.93 (1H, dd, J=11.3, 4.9 Hz), 3.82 (1H, dd, J=11.3, 4.3 Hz), 3.21 (1H, dd, =13.7, 6.1 Hz), 3.08 (1H, dd, J=13.7, 8.5 Hz), 2.71 (2H, d, J=7.2 Hz), 2.02 (3H, s). $^{13}$C-NMR (150 MHz, CDCl$_3$) δ: 170.8, 170.3, 167.2, 162.5 (d, J=245.2 Hz), 136.6, 133.5, 132.46 (d, J=3.2 Hz), 132.0, 130.59 (d, J=7.8 Hz), 129.3, 128.76, 128.69, 127.2, 127.0, 115.5 (d, J=20.8 Hz), 64.6, 54.9, 49.4, 38.3, 36.6, 20.8. TOF-ESI-MS: 485.1718 [M+Na]$^+$ (calcd. for $C_{27}H_{27}FN_2O_4$: 462.1955).

Compound 5

(S)-2-((S)-2-(4-fluorobenzamido)-3-(4-fluorophenyl)propanamido)-3-phenylpropyl acetate

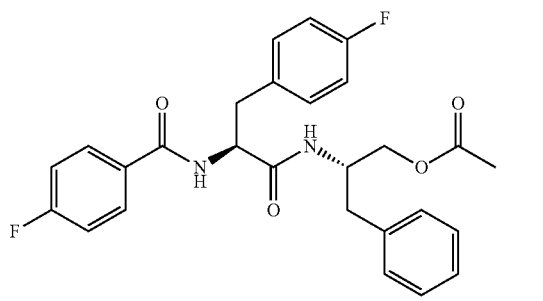

Formula (IIe)

Properties: White powders. Yield: 79%. $[α]_{25}^D$ −14.7 (c=1.77, MeOH); $^1$H-NMR (600 MHz, DMSO-d$^6$) δ: 8.58 (1H, d, J=8.4 Hz), 8.18 (1H, d, J=8.4 Hz), 7.89-7.86 (2H, m), 7.35-7.32 (2H, m), 7.30-7.28 (2H, m), 7.27-7.26 (1H, m), 7.23-7.22 (4H, m), 7.19-7.15 (1H, m), 7.09-7.06 (2H, m), 4.66-4.62 (2H, m), 4.42-4.35 (1H, m), 4.18-4.15 (1H, m), 4.01 (1H, dd, J=11.3, 4.9 Hz), 3.86 (1H, dd, J=11.3, 4.2 Hz), 2.98-2.87 (2H, m), 2.80-2.77 (2H, m), 1.99 (3H, s). $^{13}$C-NMR (150 MHz, DMSO-d$^6$) δ: 171.5, 170.8, 165.6, 165.2 (d, J=252.9 Hz), 162.2 (d, J=252.9 Hz), 138.4, 131.4 (d, J=8.9 Hz), 130.89 (d, J=2.2 Hz), 130.6 (d, J=8.9 Hz), 129.6, 129.5, 128.7, 126.7, 115.6 (d, J=22.8 Hz), 115.2 (d, J=22.8 Hz), 64.6, 55.4, 49.6, 38.4, 36.8, 21.1. TOF-ESI-MS: 503.1611 [M+Na]$^+$ (calcd. for $C_{27}H_{26}F_2N_2O_4$: 480.1861).

Compound 6

(S)-2-((S)-2-benzamido-3-(4-fluorophenyl)propanamido)-3-(4-fluorophenyl)propyl acetate Formula (IIf)

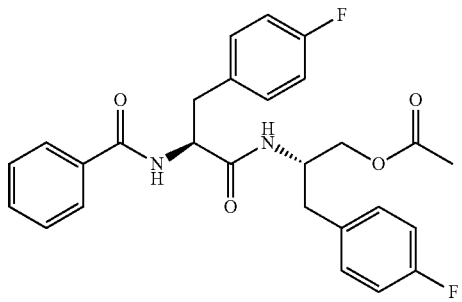

Properties: White powders. Yield: 84%. $[\alpha]_{25}^{D}$ −9.0 (c=0.54, MeOH); $^1$H-NMR (600 MHz, CDCl$_3$) δ: 7.72 (2H, d, J=7.77 Hz), 7.53 (1H, t, J=7.4b Hz), 7.44 (2H, 1, J=7.81 Hz), 7.14-7.10 (4H, m), 7.00-6.96 (4H, m), 6.83 (1H, d, J=8.4 Hz), 6.44 (1H, d, J=8.4 Hz), 4.81 (1H, dd, J=14.2, 7.3 Hz), 4.34-4.31 (1H, m), 4.04 (1H, dd, J=11.5, 4.1 Hz), 3.97 (1H, dd, J=5.2 Hz), 3.11 (2H, d, J=13.8, 4.7 Hz), 2.78 (1H, dd, J=13.9, 6.9 Hz), 2.68 (1H, dd, J=13.9, 7.6 Hz), 1.98 (3H, s). $^{13}$C-NMR (150 MHz, CDCl$_3$) δ: 171.0, 170.3, 167.2, 162.8 (d, J=252.9 Hz,), 161.1 (d, J=252.9 Hz), 133.5, 132.6 (d, J=3.0 Hz), 132.1 (d, J=2.6 Hz), 130.9 (d, J=8.9 Hz), 130.7 (d, J=8.9 Hz), 128.7, 127.0, 115.61 (d, J=22.8 Hz), 115.47 (d, J=22.8 Hz), 64.3, 54.8, 50.0, 37.4, 36.5, 20.7. TOF-ESI-MS: 503.1628 [M+Na]$^+$ (calcd for C$_{27}$H$_{26}$F$_2$N$_2$O$_4$: 480.1861).

Compound 7

(S)-2-((S)-2-(4-fluorobenzamido)-3-phenylpropanamido)-3-(4-fluorophenyl)propyl acetate Formula (IIg)

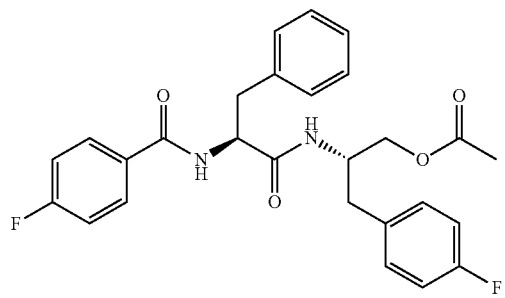

Properties: White powders. Yield: 85%. $[\alpha]_{25}^{D}$ −6.1 (c=0.98, MeOH); $^1$H-NMR (600 MHz, CDCl$_3$) δ: 7.75-7.73 (2H, m), 7.33-7.30 (2H, m), 7.27-7.26 (3H, m), 7.14 (2H, t, J=8.6 Hz), 7.07-7.04 (2H, m), 6.87 (2H, t, J=8.9 Hz), 6.77 (1H, d, J=7.5 Hz), 6.04 (1H, d, J=8.4 Hz), 4.79-4.75 (1H, m), 4.36-4.31 (1H, m), 3.95 (1H, dd, J=11.3, 4.9 Hz), 3.83 (1H, dd, J=11.3, 4.2 Hz), 3.23 (1H, dd, J=13.7, 5.9 Hz), 3.08 (1H, dd, J=13.7, 8.5 Hz), 2.74 (2H, d, J=7.2 Hz), 2.05 (3H, s). $^{13}$C-NMR (150 MHz, CDCl$_3$) δ: 170.8, 170.3, 166.1, 165.8 (d, J=252.9 Hz), 162.5 (d, J=252.9 Hz), 136.5, 132.4 (d, J=3.3 Hz), 130.6 (d, J=8.9 Hz), 129.8 (d, J=3.3 Hz), 129.4 (d, J=8.9 Hz), 129.3, 128.8, 127.2, 115.8 (d, J=22.8 Hz), 115.5 (d, J=22.8 Hz), 64.5, 55.0, 49.5, 38.4, 36.6, 20.8. TOF-ESI-MS: 503.1636 [M+Na]$^+$ (calcd for C$_{27}$H$_{26}$F$_2$N$_2$O$_4$: 480.1861).

Compound 8

(S)-2-((S)-2-(4-fluorobenzamido)-3-(4-fluorophenyl)propanamido)-3-(4-fluorophenyl)propyl acetate Formula (IIh)

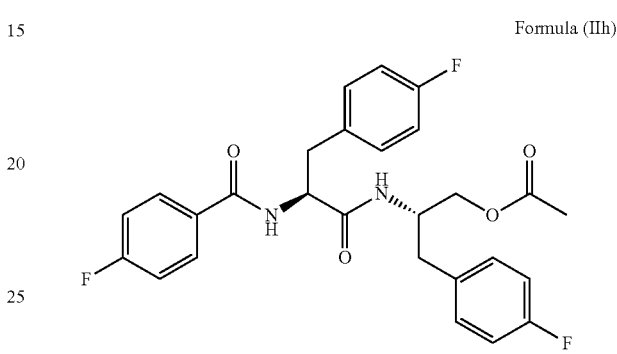

Properties: White powders. Yield; 86%. $[\alpha]_{25}^{D}$ −4.1 (c=0.32, MeOH); $^1$H-NMR (600 MHz, CDCl$_3$) δ: 7.75-7.73 (2H, m), 7.23-7.21 (2H, m), 7.17-7.14 (2H, m), 7.08-7.06 (2H, m), 7.01-6.97 (2H, m), 6.71 (1H, d, J=7.8 Hz), 6.10 (1H, d, J=8.4 Hz), 4.75-4.72 (1H, m), 4.38-4.32 (1H, m), 4.00 (1H, dd, J=13.8, 5.0 Hz), 3.92 (1H, dd, J=13.8, 4.2 Hz), 3.18 (1H, dd, J=13.8, 4.7 Hz), 3.10 (1H, dd, J=13.7, 8.5 Hz), 2.76 (2H, d, J=7.2 Hz), 2.07 (3H, s). $^{13}$C-NMR (150 MHz, CDCl$_3$) δ: 170.8, 170.1, 166.0, 165.9 (d, J=252.9 Hz), 162.8 (d, J=252.9 Hz), 162.5 (d, J=252.9 Hz), 132.3 (d, J=2.8 Hz),), 132.2 (d, J=2.8 Hz), 130.8 (d, J=8.9 Hz), 130.6 (d, J=8.9 Hz), 129.6 (d, J=2.8 Hz), 129.4 (d, J=8.9 Hz), 115.9 (d, J=22.8 Hz), 115.7 (d, J=22.8 Hz), 115.5 (d, J=22.8 Hz), 64.6, 55.0, 49.6, 37.5, 36.6, 20.7 TOF-ESI-MS: 521.1525 [M+Na]$^+$ (calcd for C$_{27}$H$_{25}$F$_3$N$_2$O$_4$: 498.1766).

Compound 9

N—((S)-1-(((S)-1-hydroxy-3-phenylpropan-2-yl)amino)-1-oxo-3-phenylpropan-2-yl)benzamide Formula (IIIa)

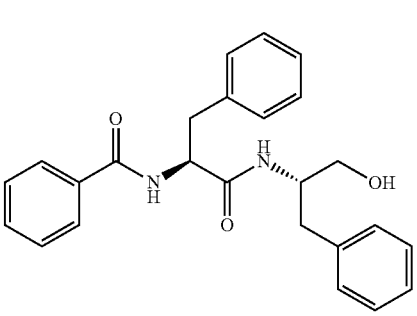

Properties: White powders. Yield: 82%. $[\alpha]_{25}^{D}$ −22.7 (c=0.44, MeOH); $^1$H-NMR (600 MHz, DMSO-d$^6$) δ: 8.49 (1H, d, J=8.4 Hz), 7.89 d, J=8.4 Hz), 7.78 (2H, d, J=7.77

Hz), 7.53 (1H, t, J=7.46 Hz), 7.45 (2H, t, J=7.81 Hz), 7.31-7.29 (2H, m), 7.24-7.22 (2H, m), 7.21-7.19 (2H, m), 7.18-7.16 (1H, m), 7.15-7.10 (1H, m), 4.86-4.83 (1H, m), 4.69-4.66 (1H, m), 3.91-3.87 (1H, m), 3.34-3.31 (1H, m), 3.29-3.25 m), 3.03 (1H, dd, J=11.3, 4.9 Hz), 2.95 (1H, dd, J=11.3, 4.2 Hz), 2.87 (1H, dd, J=13.7, 5.91 Hz), 2.67 (1H, dd, J=13.7, 8.5 Hz). $^{13}$C-NMR (150 MHz, DMSO-d$^6$) δ: 171.4, 166.6, 139.4, 138.8, 134.5, 131.8, 129.65, 129.63, 128.7, 128.53, 128.49, 127.8, 126.7, 126.4, 62.7, 55.3, 52.9, 37.7, 36.9. TOF-ESI-MS: 425.1732 [M+Na]$^+$ (calcd. for C$_{25}$H$_{26}$N$_2$O$_3$:402.1943).

Compound 10

N—((S)-3-(4-fluorophenyl)-1-(((S)-1-hydroxy-3-phenylpropan-2-yl)amino)-1-oxopropan-2-yl)benzamide

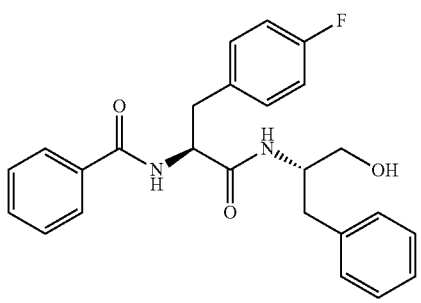

Formula (IIIb)

Properties: white powders. Yield: 78%. $[α]_{25}^D$ −8.0 (c=0.30, MeOH); $^1$H-NMR (600 MHz, CDCl$_3$) δ: 7.70 (2H, d, J=7.77 Hz), 7.52 (1H, t, J=7.46 Hz), 7.41 (2H, t, J=7.81 Hz), 7.37-7.25 (2H, m), 7.22-7.19 (2H, m), 7.14-7.10 (1H, m), 7.05-7.02 (2H, m), 7.00 (1H, d, J=8.4 Hz), 6.92-6.89 (2H, m), 6.59 (1H, d, J=8.4 Hz), 4.82-4.79 (1H, m), 4.19-4.14 (1H, m), 3.67 (1H, dd, J=11.3, 4.9 Hz), 3.50 (1H, dd, J=11.3, 4.2 Hz), 3.07 (1H, dd, J=13.8, 7.26 Hz), 3.02 (1H, dd, J=13.8, 6.39 Hz), 2.77-2.71 (2H, m). $^{13}$C-NMR (150 MHz, CDCl$_3$) δ: 171.1, 167.6, 162.8 (d, J=255 Hz), 137.5, 133.4, 132.1, 132.0 (d, J=3.3 Hz), 130.9 (d, J=7.8 Hz), 129.2, 128.7, 128.6, 127.1, 126.8, 115.5 (d, J=22.8 Hz), 63.8, 55.3, 53.0, 37.7, 36.9. TOF-ESI-MS: 419.1917 [M-H]$^-$ (calcd for C$_{25}$H$_{25}$FN$_2$O$_3$; 420.1849).

Compound 11

4-fluoro-N—((S)-1-(((S)-1-hydroxy-3-phenylpropan-2-yl)amino)-1-oxo-3-phenylpropan-2-yl)benzamide

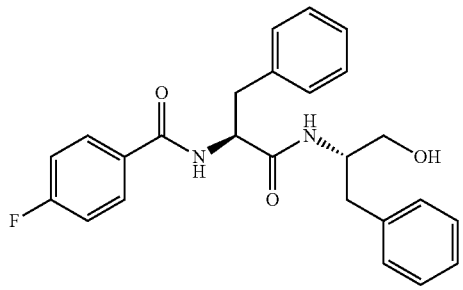

Formula (IIIc)

Properties: White powders. Yield: 81%. $[α]_{25}^D$ −3.8 (c=1.62, MeOH); $^1$H-NMR (600 MHz, DMSO-d$^6$) δ: 8.56 (1H, d, J=8.4 Hz), 7.90 (1H, d, J=8.4 Hz), 7.87-7.86 (2H, m), 7.32-7.31 (2H, m), 7.31-7.27 (2H, m), 7.26-7.23 (2H, m), 7.22-7.21 (2H, m), 7.20-7.18 (2H, m), 7.17-7.12 (2H, m), 4.83 (1H, t, J=5.5 Hz), 4.69-4.65 (1H, m), 3.93-3.88 (1H, m), 3.35-3.31 m), 3.29-3.26 (1H, m), 3.05 (1H, dd, J=13.8, 4.0 Hz), 2.96 (1H, dd, J=13.8, 8.6 Hz), 2.88 (1H, dd, J=13.8, 6.0 Hz), 2.68 (1H, dd, J=13.8, 8.0 Hz). $^{13}$C-NMR (150 MHz, DMSO-d$^6$) δ: 171.4, 165.5, 165.2 (d, J=249.3 Hz), 139.4, 138.8, 131.0 (d, J=2.6 Hz), 130.6 (d, J=7.8 Hz), 129.64, 129.62, 126.65, 126.49, 115.6 (d, J=21.2 Hz), 62.7, 55.3, 52.9, 37.7, 36.9. TOF-ESI-MS: 443.1654 [M+Na]$^+$ (calcd for C$_{25}$H$_{25}$FN$_2$O$_3$: 420.1849).

Compound 12

N—((S)-1-(((S)-1-(4-fluorophenyl)-3-hydroxypropan-2-yl)amino)-1-oxo-3-phenylpropan-2-yl)benzamide

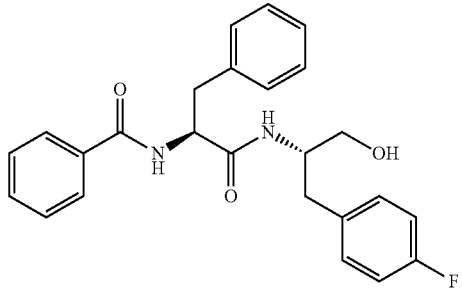

Formula (IIId)

Properties: White powders. Yield: 80%, $[α]_{25}^D$ −8.0 (c=0.89, MeOH); $^1$H-NMR (600 MHz, DMSO-d$^6$) δ: 8.56 (1H, d, J=8.4 Hz), 7.90 (1H, d, J=8.4 Hz), 7.80-7.79 (2H, m), 7.53 (1H, t, J=7.46 Hz), 7.47-7.44 (2H, m), 7.31 (2H, d, J=7.3 Hz), 7.26-7.24 (2H, m), 7.23-7.22 (2H, m), 7.17-7.15 (1H, m), 6.98-6.95 (2H, m), 4.83 (1H, t, J=5.5 Hz), 4.69-4.65 (1H, m), 3.90-3.85 m), 3.34-3.32 (1H, m), 3.30-3.26 (1H, m), 3.03 (1H, dd, J=11.3, 4.9 Hz), 2.97 (1H, dd, J=11.3, 4.2 Hz), 2.88 (1H, dd, J=13.7, 5.91 Hz), 2.65 (1H, dd, J=13.7, 8.5 Hz). $^{13}$C-NMR (150 MHz, DMSO-d$^6$) δ: 171.4, 166.5, 162.0 (d, J=241.2 Hz), 138.8, 135.5 (d, J=3.2 Hz), 134.5, 131.8, 131.4 (d, J=7.6 Hz), 129.6, 128.65, 128.49, 127.9 126.7, 115.2 (d, J=20.6 Hz), 62.7, 55.3, 52.9, 37.6, 36.0. TOF-ESI-MS: 443.1620 (M-H) (calcd. for $C_{25}H_{25}FN_2O_3$: 420.1849).

Compound 13

4-fluoro-N—((S)-3-(4-fluorophenyl)-1-(((S)-1-hydroxy-3-phenylpropan-2-yl)amino-1-oxopropan-2-yl)benzamide Formula (IIIe)

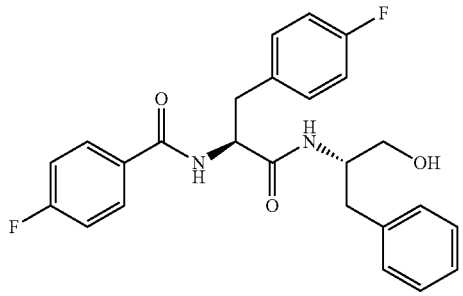

Properties: White powders. Yield: 70%. $[\alpha]_{25}^D$ −20.9 (c=0.67, MeOH); $^1$H-NMR (600 MHz, DMSO-d$^6$) δ: 8.54 (1H, d, J=8.4 Hz), 7.90 (1H, d, J=8.4 Hz), 7.87-7.85 (2H, m), 7.34-7.31 (2H, m), 7.30-7.28 (2H, m), 7.25-7.24 (1H, m), 7.22-7.20 (2H, m), 7.19-7.17 (2H, m), 7.14-7.12 (1H, m), 7.07-7.05 (2H, m), 4.83 (1H, t, J=5.5 Hr), 4.67-4.63 (1H, m), 3.92-3.87 (1H, m), 3.34-3.31 (1H, m), 3.29-3.26 (1H, m), 3.03 (1H, dd, J=13.7, 5.91 Hz), 2.94 (1H, dd, J=13.7, 8.5 Hz), 2.87 (1H, dd, J=13.7, 5.6 Hz), 2.68 (1H, dd, J=13.7, 8.0 Hz). $^{13}$C-NMR (150 MHz, DMSO-d$^6$) δ: 171.3, 166.3, 165.2 (d, J=252.9 Hz), 162.2 (d, J=252.9 Hz), 139.4, 131.4 (d, J=8.9 Hz), 130.9 (d, J=2.2 Hz), 130.5 (d, J=8.9 Hz), 129.6, 129.5, 128.7, 128.5, 126.7, 115.6 (d, J=22.8 Hz), 115.2 (d, J=22.8 Hz), 62.6, 55.4, 53.0, 38.4, 36.8. TOF-ESI-MS: 461.1528 [M+Na]$^+$ (calcd. for $C_{25}H_{24}F_2N_2O_4$: 438.1755).

Compound 14

N—((S)-3-(4-fluorophenyl)-1-(((S)-1-(4-fluorophenyl)-3-hydroxypropan-2-yl)amino)-1-oxopropan-2-yl)benzamide Formula (IIIf)

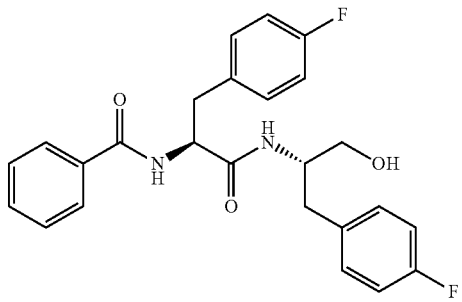

Properties: White powders. Yield: 73%. $[\alpha]_{25}^D$ −3.8 (c=0.72, MeOH); $^1$H-NMR (600 MHz, CDCl$_3$) δ: 7.72 (2H, d, J=7.77 Hz), 7.57 (1H, t, J=7.46 Hz), 7.48 (2H, t, J=7.81 Hz), 7.25-7.23 (2H, m), 7.11-7.08 (2H, m), 7.01 (2H, t, J=15.7 Hz), 6.86 (2H, t, J=15.8 Hz), 6.73 (1H, d, J=8.4 Hz), 6.17 (1H, d, J=8.4 Hz), 4.79-4.75 (1H, m), 4.13-4.11 (1H, m), 4.05 (1H, dd, J=11.5, 4.1 Hz), 3.21 (1H, dd, J=13.8, 6.1 Hz), 3.13 (1H, dd, J=13.9, 8.2 Hz), 2.83 (1H, dd, J=13.8, 7.1 Hz), 2.74 (1H, dd, J=14.0, 7.5 Hz). $^{13}$C-NMR (150 MHz, CDCl$_3$) δ: 170.7, 167.3, 161.2 (d, J=252.9 Hz), 160.8 (d, J=252.9 Hz), 133.3, 132.95 (d, J=4.0 Hz), 132.25 (d, J=3.2 Hz), 132.15, 130.9 (d, J=8.9 Hz), 130.6 (d, J=8.9 Hz), 128.8, 127.0, 115.7 (d, J=22.8 Hz), 115.4 (d, J=22.8 Hz), 63.6, 55.1, 52.8, 37.4, 36.1 TOF-ESI-MS: 461.1518 [M+Na]$^+$ (calcd for $C_{25}H_{24}F_2N_2O_4$: 438.1755).

Compound 15

4-fluoro-N—((S)-1-(((S)-1-(4-fluorophenyl)-3-hydroxypropan-2-yl)amino)-1-oxo-3-phenylpropan-2-yl)benzamide Formula (IIIg)

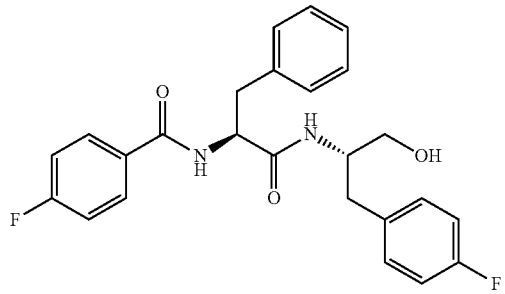

Properties: White powders. Yield: 73%. $[\alpha]_{25}^D$ −13.9 (c=0.72, MeOH); $^1$H-NMR (600 MHz, DMSO-d$^6$) δ: 8.56 (1H, d, J=8.4 Hz), 7.90 (1H, d, J=8.4 Hz), 7.88-7.85 (2H, m), 7.32-7.31 (2H, m), 7.30-7.28 (3H, m), 7.26-7.22 (4H, m), 7.17-7.15 m), 6.98-6.95 (2H, m), 4.83 (1H, t, J=5.5 Hz), 4.68-4.64 (1H, m), 3.90-3.86 (1H, m), 3.34-3.31 (1H, m), 3.29-3.25 (1H, m), 3.02 (1H, dd, J=13.8, 4.6 Hz), 2.94 (1H, dd, J=13.7, 4.9 Hz), 2.87 (1H, dd, J=13.7, 5.3 Hz), 2.65 (1H, dd, J=13.7, 8.5 Hz). $^{13}$C-NMR (150 MHz, DMSO-d$^6$) δ: 171.4, 165.5, 165.2 (d, J=252.9 Hz), 162.0 (d, J=252.9 Hz), 138.8, 135.5, 131.4 (d, J=8.9 Hz), 130.9, 130.6 (d, J=8.9 Hz), 129.6, 128.5, 126.7, 115.7 (d, J=22.8 Hz), 115.2 (d, J=22.8 Hz), 62.7, 55.3, 52.9, 37.6, 36.0. TOF-ESI-MS: 461.1525 [M+Na]$^+$ (calcd for $C_{25}H_{24}F_2N_2O_4$:438.1755).

Compound 16

4-fluoro-N—((S)-3-(4-fluorophenyl)-1-(((S)-1-(4-fluorophenyl)-3-hydroxypropan-2-yl)amino)-1-oxo-propan-2-yl)benzamide Formula (IIIh)

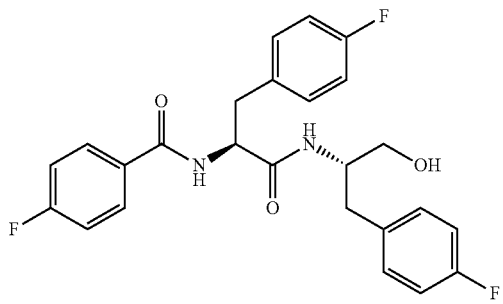

Properties: White powders. Yield: 80%. $[\alpha]_{25}^D$ −6.7 (c=0.21, MeOH); $^1$H-NMR (600 MHz, DMSO-d$^6$) δ: 8.55 (1H, d, J=8.4 Hz), 7.91 (1H, d, J=8.4 Hz), 7.88-7.86 (2H, m), 7.35-7.32 (2H, m), 7.31-7.28 (2H, m), 7.24-7.22 (2H, m), 7.07 (2H, m), 6.97 (2H, m), 4.84-4.82 (1H, m), 4.66-4.61 (1H, m), 3.90-3.86 (1H, m), 3.31-3.25 (1H, m), 3.01 (1H, dd, J=13.8, 4.7 Hz), 2.92 (1H, dd, J=13.7, 8.5 Hz), 2.88 (1H, 13.8, 4.7 Hz), 2.65 (1H, dd, J=13.8, 4.7 Hz). $^{13}$C-NMR (150 MHz, DMSO-d$^6$) δ: 171.2, 165.5, 165.2 (d, J=252.9 Hz), 162.1 (d, J=252.9 Hz), 162.0 (d, J=252.9 Hz), 135.5 (d, J=2.8 Hz), 134.9 (d, J=2.8 Hz), 131.44 (d, J=8.9 Hz), 131.40 (d, J=8.9 Hz), 130.9 (d, J=2.8 Hz), 130.5 (d, J=8.9 Hz), 115.7 (d, J=22.8 Hz), 115.3 (d, J=22.8 Hz), 115.2 (d, J=22.8 Hz), 62.7, 55.3, 52.9, 36.8, 36.0. TOF-ESI-MS: 479.1419 [M+Na]$^+$ (calcd for $C_{25}H_{23}F_3N_2O_4$: 456.1661).

Example 2

Preparation of an Influenza Virus

Human Embryonic Kidney 293 (HEK293) cells Madin-Darby canine kidney (MDCK) cells were purchased from ATCC and cultured in DMEM medium (Hyclone), supplemented with in % fetal bovine serum (FBS) at 37° C.

A/PR/8/34 (H1N1) viruses were propagated in the allantoic cavities of chicken eggs and titrated on monolayers of Madin-Darby Canine Kidney (MDCK) cells. Briefly, monolayers of MDCK cells (5×10$^6$ cells/well) were seeded in 96-well tissue culture plates and infected with 10-fold serial dilutions of the virus stocks in serum-free DMEM, which were supplemented with 2 μg/mL of L-1-tosylamide-2-phenylethyl chloromethyl ketone (TPCK)-treated trypsin. The cytopathic effect of MDCK cells were inspected under a microscope at 48 h post-infection (p.i.).

Example 3

Determination of Anti-Influenza Activity of the Compounds

The antiviral effects of the compounds were determined by cytopathic effect (CPE) inhibition assay in MDCK cells. Confluent monolayers of MDCK cells in 96-well plates were inoculated with 100TCID$_{50}$ of influenza virus for 2 h, after which the inoculum was removed and the cells were incubated with different concentrations of the compound diluted in TPCK-trypsin containing medium, i.e. at a concentration of 1000 μg/ml, 500 μg/ml, 250 μg/ml, 125 μg/ml, 62.5 μg/ml, 31.25 μg/ml, or 15.625 μg/ml, for 48 h. The CPE was determined via microscopy and the concentration required to inhibit virus-induced CPE by 50% (IC$_{50}$) was calculated by the Reed-Muench method. The Reed-Muench method is as described in American journal of Epidemiology 1938, 27, 493-497. The results were obtained from three independent experiments. The SI (selectivity index) was calculated as the ratio of TC$_{50}$ to IC$_{50}$. The results are presented in Table 1.

TABLE 1

| Antiviral effect of the compounds in Example 1 against influenza A H1N1 | | |
|---|---|---|
| Compound No. | IC$_{50}$ (μM) | SI |
| 1 | 74.3 | >12.2 |
| 2 | 39.6 | >8.5 |
| 3 | 42.4 | >8.0 |
| 4 | 29.6 | >11.4 |
| 5 | 37.9 | >8.6 |
| 6 | 19.2 | >16.9 |
| 7 | 13.5 | >24.1 |
| 8 | 5.8 | >60.6 |
| 9 | 34.0 | >11.4 |
| 10 | 14.3 | >26.0 |
| 11 | 47.0 | >7.9 |
| 12 | 17.4 | >21.3 |
| 13 | 10.5 | >34.1 |
| 14 | 19.7 | >18.1 |
| 15 | 38.7 | >9.2 |
| 16 | 5.2 | >59.0 |

As shown in Table 1, all compounds demonstrated good anti-influenza virus effect. Especially, Compounds 8 and 16 demonstrated the most effective activity against A/PR/8/34 virus with IC$_{50}$ value below 6.0 μM and 10-fold more efficient than Compound 1 and 9 respectively. The results show that the introduction of para-fluorine on the three phenyl rings in Compound 8 and Compound 16 substantially improves the anti-influenza A virus activity. Both Compound 8 and Compound 16 achieve a similar antiviral effect which may imply that the acetate group in Compound 8 does not contribute to any significant difference on the effect.

Compared to Compounds 8 and 16, compounds having two fluorine atoms, i.e. Compounds 5-7, 13-15 show a slightly weaker effect. It is thus believed that compounds having more para-fluorinate rings can achieve a better anti-viral effect. Further, Compounds 9 to 16, i.e. aurantiamide and its analogs, generally have a better anti-viral effect than Compounds 1 to 8, i.e. aurantiamide acetate and its analogs. This illustrates that the presence of aliphatic acid in the compound may contribute to the enhanced anti-viral activity of the compound.

For the compounds having two fluorine atoms Compounds 5-7, most of them showed a better antivirus effect than mono-fluorinated compound, i.e. Compounds 2-4. In general, all Compounds 2-8 show a much better antiviral effect compared to Compound 1.

These results may relate to fluorine's ability to modulate electronic, lipophilic, and steric parameters that can critically influence the pharmacological properties of a potential drug molecule. The presence of fluorine atoms renders the compound to achieve a much better biological activity. It is believed that the fluorinated compounds, i.e. compounds having at least one fluorine atom, has better resistance to metabolism, increased lipophilicity, and enhanced activity.

Further experiments were conducted to determine whether the compounds have any effect on NF-κB pathway which has been found to be involved in influenza A virus replication. NF-κB is a dimeric transcriptional factor which plays a crucial role in the immediate early pathogen responses and regulates varieties of cellular processes such as inflammation, cellular proliferation, and differentiation. The NF-κB is essential for efficient viral replication.

Experiments were performed in vitro and in vivo to demonstrate that NF-κB signalling inhibition by the inhibitors 11-7085 or acetylsalicyclic acid (ASA) resulted in a dramatic reduction of influenza virus titers. Particularly, NF-κB—Driven Luciferase Reporter Assay was conducted to determine the inhibitory effects of the compounds on TNF-a-induced the transcriptional activity of NF-κB.

Figure 2:
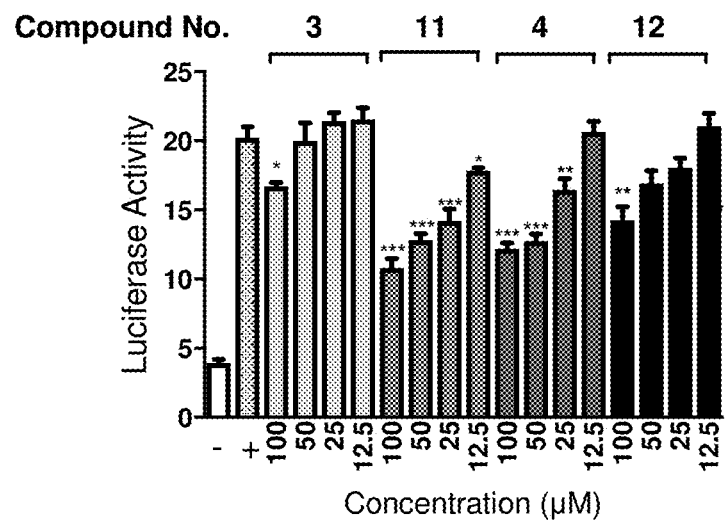
FIG. 2 is a plot showing the luciferase activity of TNF-α-induced HEK293 cells treated respectively with Compound 3, Compound 4, Compound 11 and Compound 12 at a concentration of 100 μM, 50 μM, 25 μM, or 12.5 μM, *p<0.05, p<0.01, *p<0.001, compared to TNF-a-treated alone.
Figure 3:
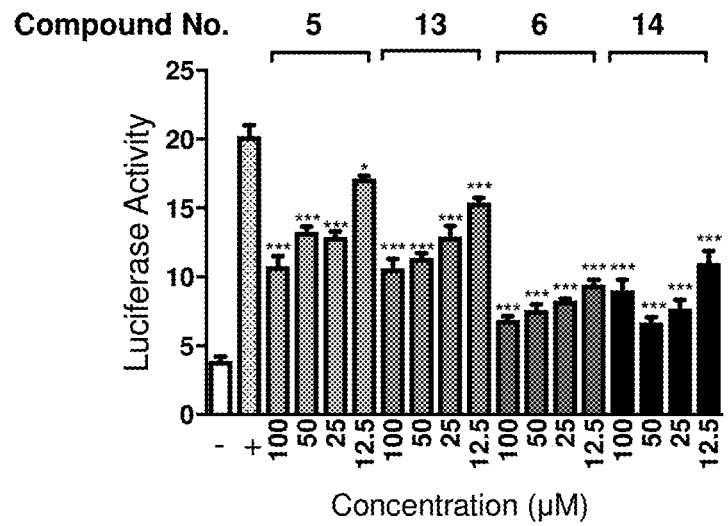
FIG. 3 is a plot showing the luciferase activity of TNF-α-induced HEK293 cells treated respectively with Compound 5, Compound 6, Compound 13 and Compound 14 at a concentration of 100 μM, 50 μM, 25 μM, or 12.5 μM, *p<0.05p<0.01, *p<0.001, compared to TNF-a-treated alone.
Figure 4:
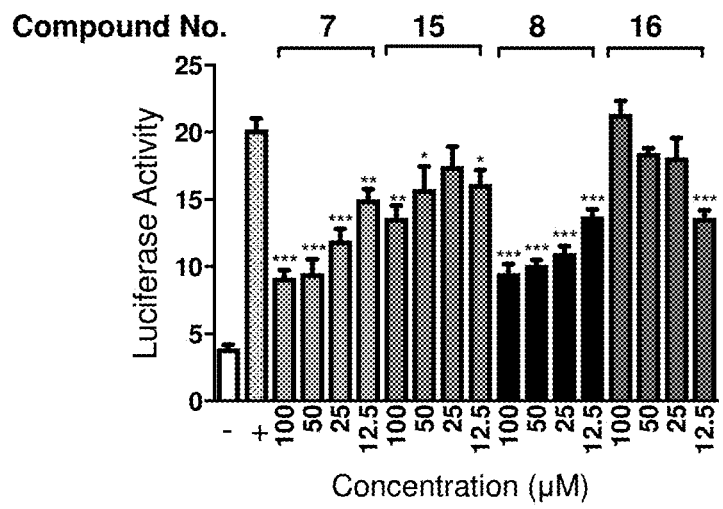
FIG. 4 is a plot showing the luciferase activity of TNF-α-induced HEK293 cells treated respectively with Compound 7, Compound 8, Compound 15 and Compound 16 at a concentration of 100 μM, 50 μM, 25 μM, or 12.5 μM, *p<0.05, p<0.01, *p<0.001, compared to TNF-a-treated alone.

HEK293 cell lines with a stably transfected NF-κB luciferase reporter plasmid were seeded in a 96-well plate at a concentration of $5 \times 10^6$/well. Then cells were stimulated with 20 ng/mL of TNF-α in the presence or absence of Compounds 1-16 for next 24 h. In particular, the cells were incubated with the compound at a concentration of 100 μM, 50 μM, 25 μM, or 12.5 μM for 24 h. At 24 h, cells were lysed for quantification of luciferase activity. After the supernatants were removed, NF-κB activity was measured according to the manufacturer's instructions using a microplate reader (Luciferase Assay System, Promega). The relative luciferase activity was then calculated and presented in FIGS. 1 to 4.

As shown in FIGS. 1 to 4, all of the compounds show the inhibition towards NF-κB activation. Compounds 6 and 14, fluorinated on para-phenyl ring of phenylalanine and phenylalaninol, show the strongest inhibition effect towards NF-κB activation. Compound 10, mono-fluorinated phenyl ring of phenylalanine, exhibits potent inhibitory effect on both the influenza A virus and the NF-κB signalling pathway.

In conclusion, all the Compounds, i.e. Compounds 2-8 and 10-16, are found to be useful in treating influenza, particularly infections caused by influenza A virus. Among them, Compounds 7, 8, 10, 13 and 16 exhibited potent anti-influenza A virus activity (with $IC_{50}$ below 14.3 μM) and Compounds 6, 10 and 14 exhibited strong inhibitory effect on NF-κB activation. Compound 10 exhibited excellent inhibitory effects on both influenza A viruses (IAV, $IC_{50}$=14.3 μM) and NF-κB signaling pathway. These compounds are useful in developing anti-influenza agents.

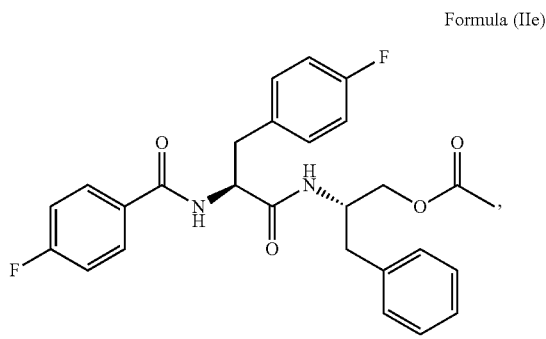

Formula (IIf)
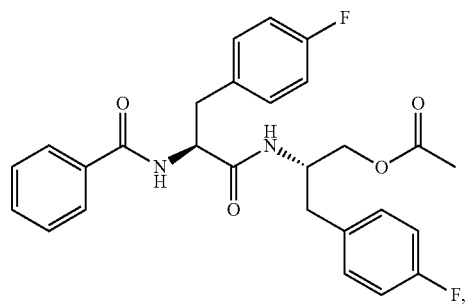
Formula (IIg)
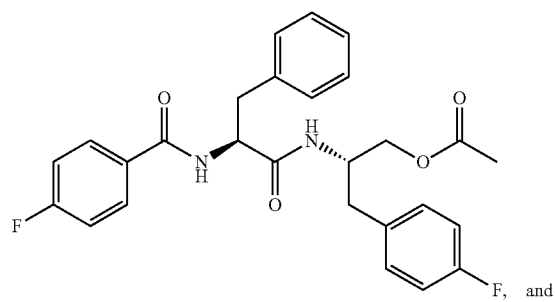
and
Formula (IIh)
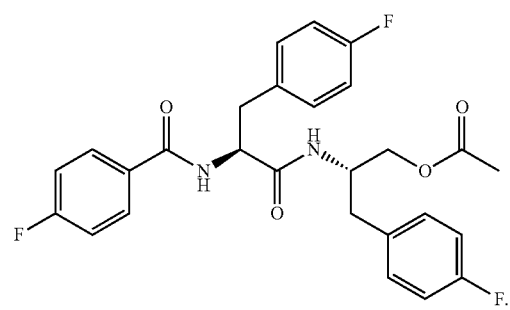
27. The method of claim 26, wherein the compound is further subjected to ester hydrolysis to produce the compound having a structure of Formula (IIIb) to (IIIh),
Formula (IIIb)
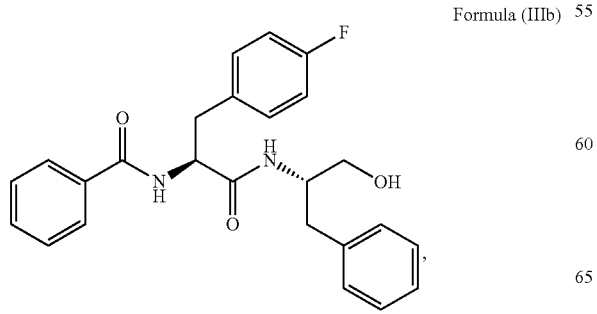
Formula (IIIc)
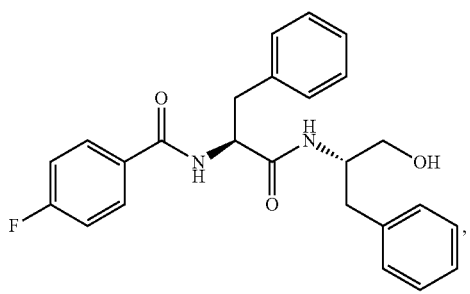
Formula (IIId)
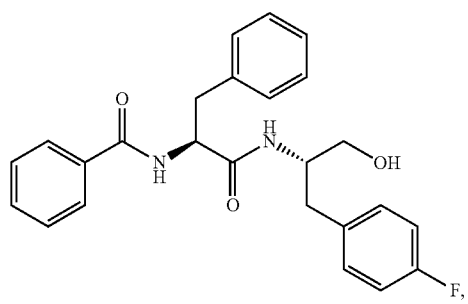
Formula (IIIe)
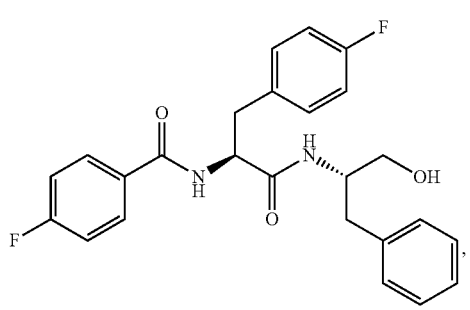
Formula (IIIf)
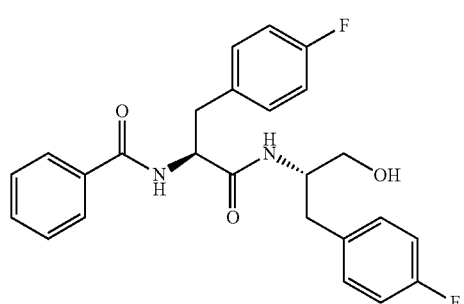
Formula (IIIg)
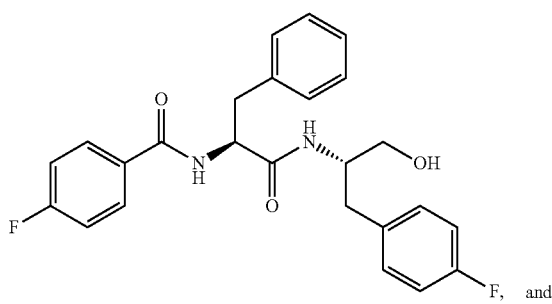
and Formula (IIIh)
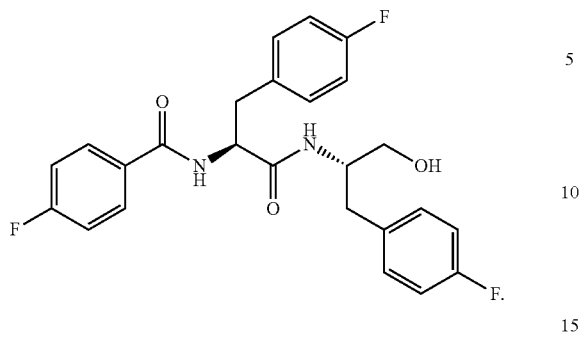

The invention claimed is:

1. A compound comprising a structure of Formula (I)

Formula (I)

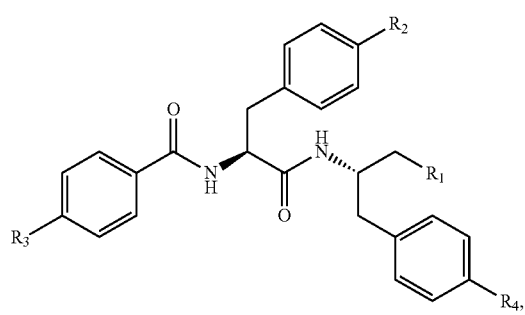

wherein $R_1$ is —OH, —CH$_2$OH, or —OCOCH$_3$;
$R_2$, $R_3$, and $R_4$ are independently —H, —CH$_3$ or —F, and at least one of $R_2$ and $R_4$ is —F.

2. The compound of claim 1, wherein $R_1$ is —OH, or —OCOCH$_3$.

3. The compound of claim 1, wherein at least two of $R_2$, $R_3$, and $R_4$ are —F.

4. The compound of claim 1, wherein $R_2$, $R_3$, and $R_4$ are simultaneously —F.

5. The compound of claim 1, wherein the compound has a structure selected from the group consisting of Formula (IIb) to Formula (IIh)

Formula (IIb)

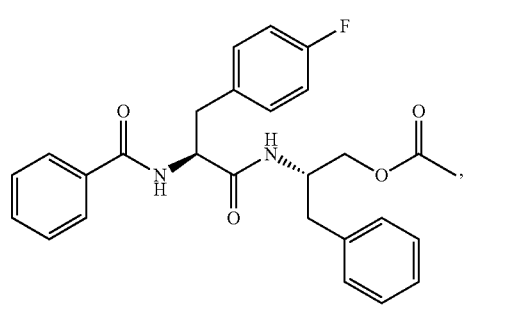

,

Formula (IIc)

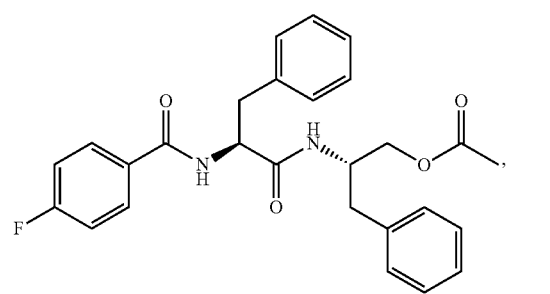

,

Formula (IId)

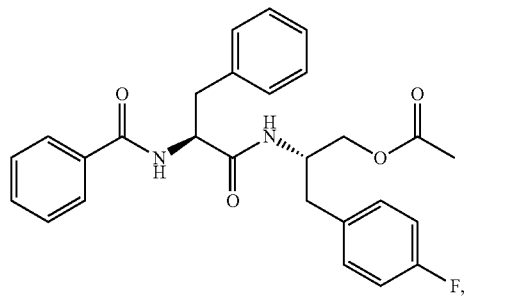

,

Formula (IIe)

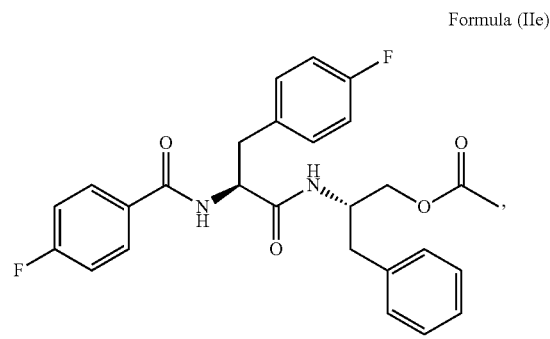

,

Formula (IIf)
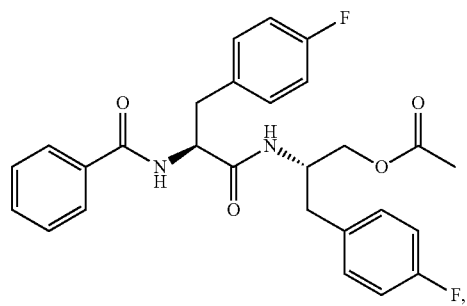
Formula (IIg)
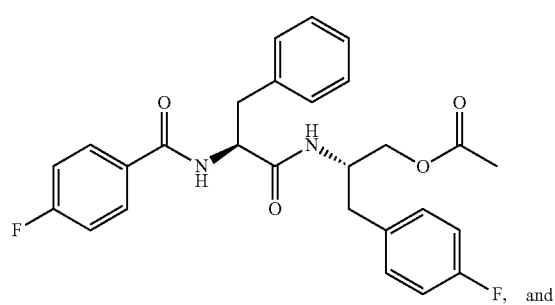
and
Formula (IIh)
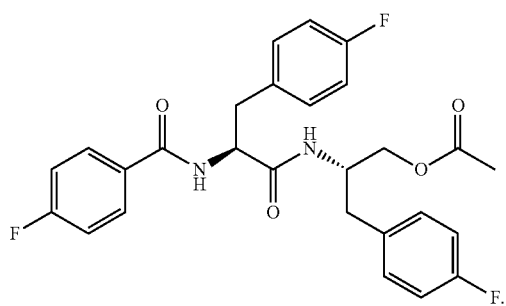
6. The compound of claim 1, wherein the compound has a structure selected from the group consisting of Formula (IIIb) and Formula (IIId) to Formula (IIIh)
Formula (IIIb)
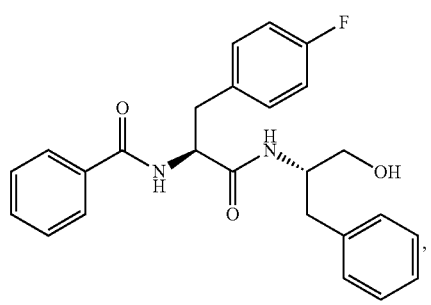
,
Formula (IIId)
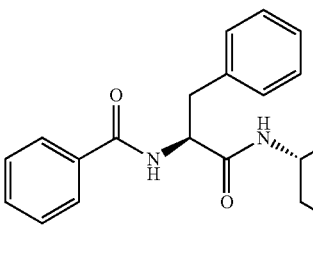
,
Formula (IIIe)
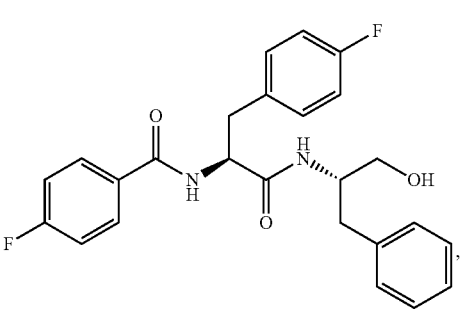
,
Formula (IIIf)
Formula (IIIg)
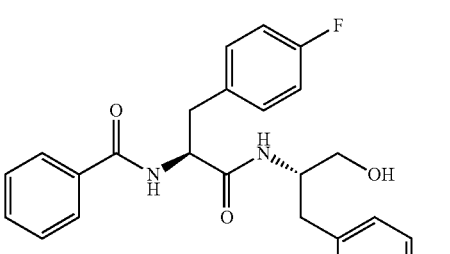
,
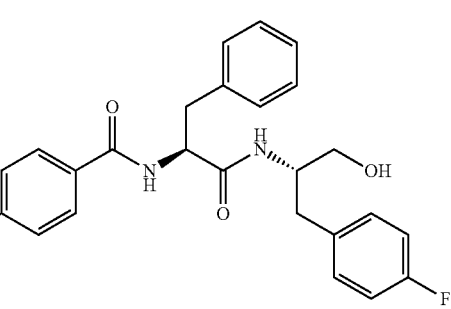
, and
Formula (IIIh)

7. The compound of claim 1, where the compound has a structure of Formula (IIf) or (IIIf)

Formula (IIf)

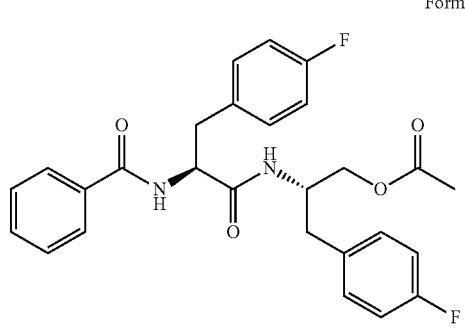

Formula (IIIf)

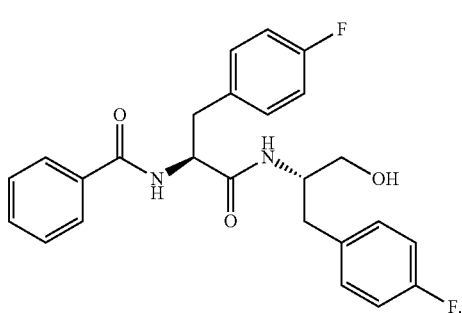

8. The compound of claim 1, where the compound has a structure of Formula (IIh) or (IIIh)

Formula (IIh)

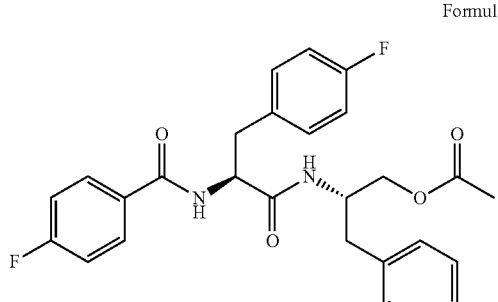

Formula (IIIh)

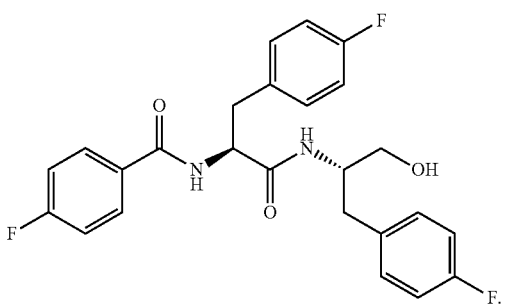

9. A method of treating a subject suffering from a viral disease comprising administering an effective amount of a compound comprising a structure of Formula (I) or a solvate thereof to the subject, Formula (I)

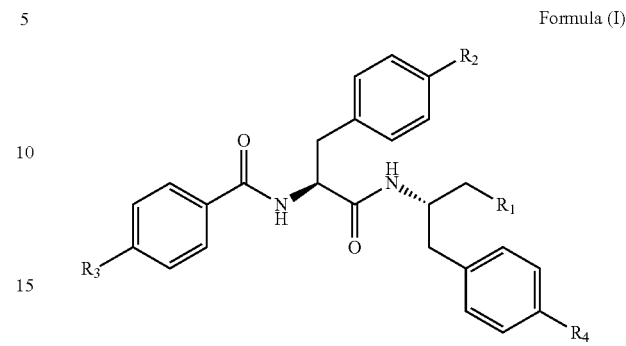

wherein $R_1$ being —OH, —CH$_2$OH, or —OCOCH$_3$;
$R_2$, $R_3$, and $R_4$ being independently —H, —CH$_3$ or —F, and at least one of $R_2$ and $R_4$ is —F.

10. The method of claim 9, wherein the viral disease is influenza.

11. The method of claim 10, wherein the influenza is caused by influenza virus A.

12. The method of claim 10, wherein the influenza is caused by influenza virus A subtype H1N1.

13. The method of claim 9, wherein $R_1$ is —OH, or —OCOCH$_3$.

14. The method of claim 9, wherein at least two of $R_2$, $R_3$, and $R_4$ are —F.

15. The method of claim 9, wherein $R_2$, $R_3$, and $R_4$ are simultaneously —F.

16. The method of claim 9, wherein the compound has a structure selected from the group consisting of Formula (IIb) to Formula (IIh)

Formula (IIb)

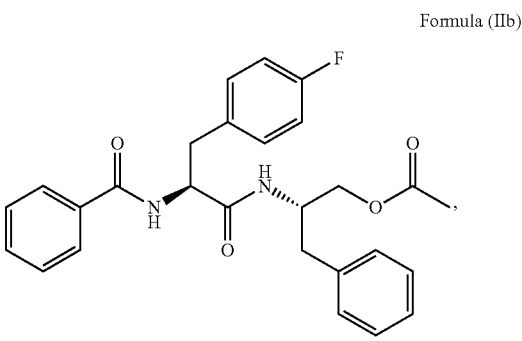

Formula (IIc)

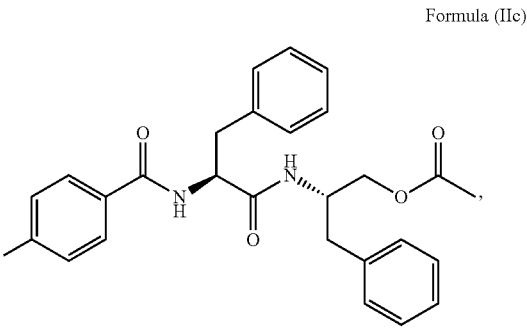

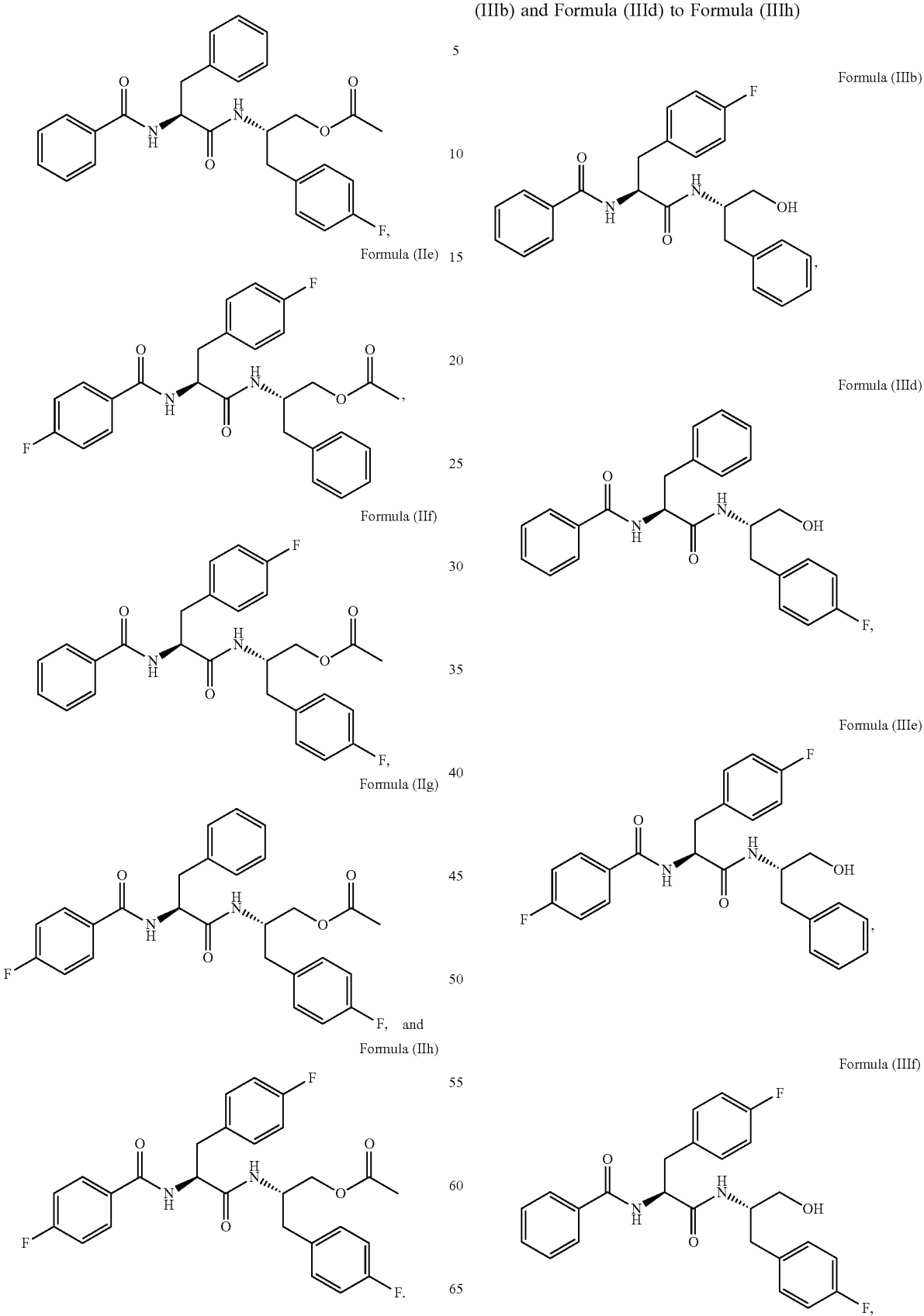
17. The method of claim 9, wherein the compound has a structure selected from the group consisting of Formula (IIIb) and Formula (IIId) to Formula (IIIh)

Formula (IIIg)

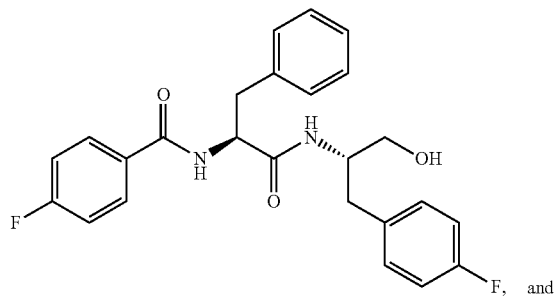

F, and

Formula (IIIh)

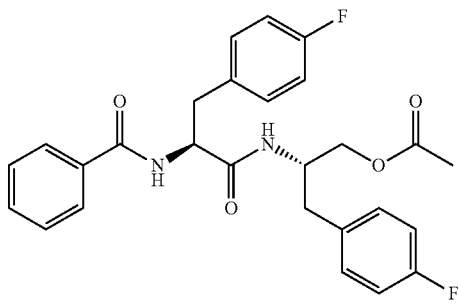

F.

18. The method of claim 9, where the compound has a structure of Formula (IIf) or (IIIf)

Formula (IIf)

Formula (IIIf)

19. The method of claim 9, where the compound has a structure of Formula (IIh) or (IIIh)

Formula (IIh)

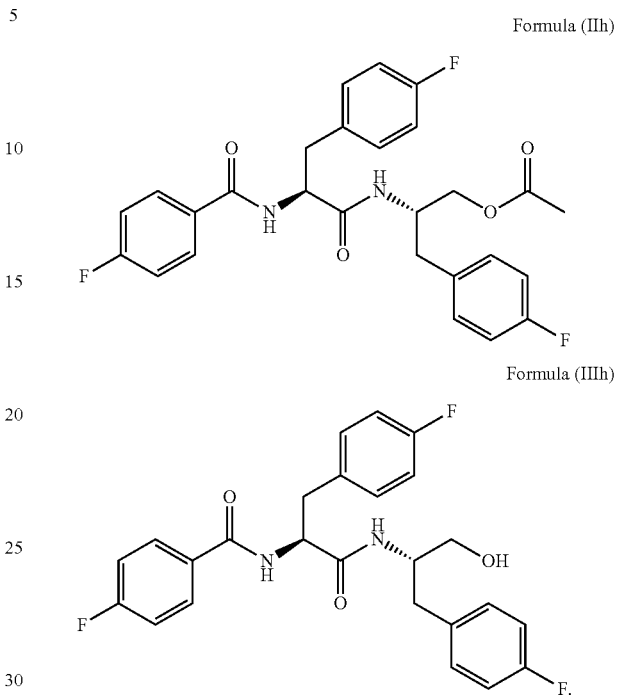

Formula (IIIh)

20. A method of preparing a compound, comprising steps of:

a) contacting a N-tert-butoxycarbonyl-protected amino acid (N-Boc-protected amino acid) of Formula (IV) with an amino alcohol of Formula (V), optionally in the presence of a coupling agent, under suitable condition to form a first intermediate of Formula (VI), Formula (IV)

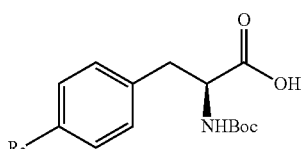

Formula (V)

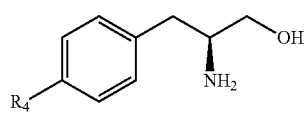

Formula (VI)

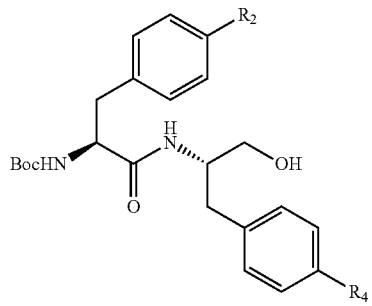

wherein R₂ and R₄ are independently —H, —CH₃ or —F,
b) converting the first intermediate into an ester;
c) removing a Boc group from the ester of the step b) to form a second intermediate; and
d) contacting the second intermediate with a substituted or unsubstituted benzoyl chloride of Formula (VII) to form the compound Formula (VII)

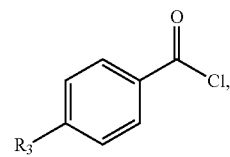

wherein R₃ is —H, —CH₃ or —F.

21. The method of claim 20, wherein the compound has a structure of Formula (I) with R₁ being —OH, or —OCOCH₃, and R₂, R₃, and R₄ being independently —H, —CH₃ or —F, and wherein at least one of R₂, R₃, and R₄ is —F Formula (I)

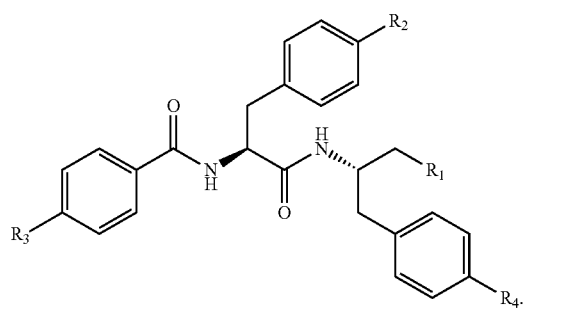

22. The method of claim 20, wherein the coupling agent is 1-ethyl-3-(3-dimethylaminopropyl) carbodiimide and/or hydroxybenzotriazole.

23. The method of claim 20, wherein in the step b), the first intermediate is converted into an ester of Formula (VIII) by contacting with a carboxylic acid anhydride Formula (VIII)

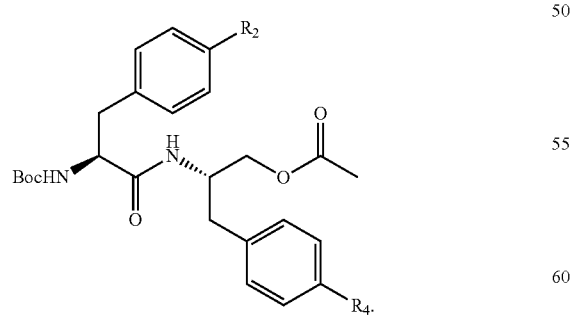

24. The method of claim 20, in the step c), the Boc group is removed by using an acid.

25. The method of claim 24, wherein the acid is perfluorinative carboxylic acid.

26. The method of claim 20, wherein the compound has a structure selected from Formula (IIb) to (IIh), Formula (IIb)

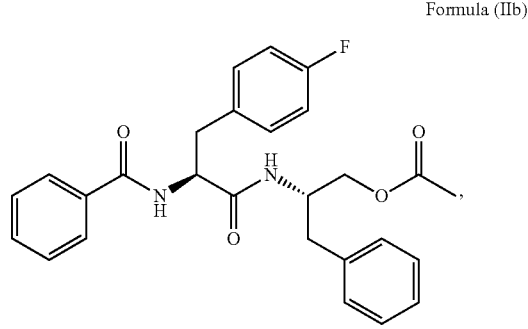

Formula (IIc)

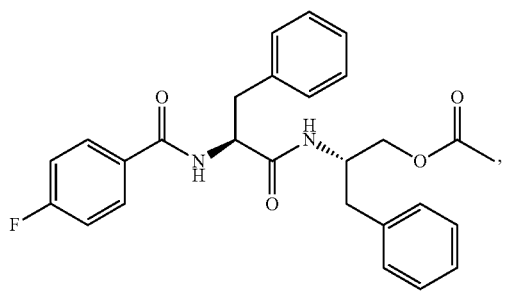

Formula (IId)

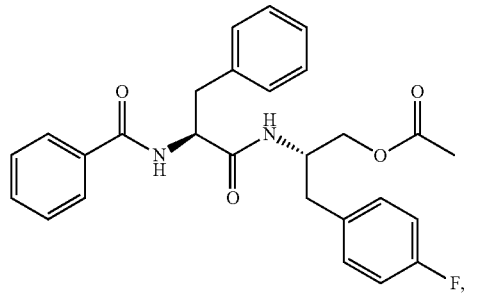

Formula (IIe)